US012642656B2

(12) United States Patent
Kim

(10) Patent No.: US 12,642,656 B2
(45) Date of Patent: Jun. 2, 2026

(54) TRANSCATHETER SYSTEM AND METHOD FOR REDUCING TRICUSPID REGURGITATION

(71) Applicant: TAU MEDICAL INC., Yangsan-si (KR)

(72) Inventor: June-Hong Kim, Busan (KR)

(73) Assignee: TAU MEDICAL INC, Busan (KR)

( * ) Notice: Subject to any disclaimer, the term of this patent is extended or adjusted under 35 U.S.C. 154(b) by 844 days.

(21) Appl. No.: 17/800,741

(22) PCT Filed: Feb. 20, 2021

(86) PCT No.: PCT/US2021/018942
§ 371 (c)(1),
(2) Date: Aug. 18, 2022

(87) PCT Pub. No.: WO2021/168381
PCT Pub. Date: Aug. 26, 2021

(65) Prior Publication Data
US 2023/0099085 A1     Mar. 30, 2023

Related U.S. Application Data

(60) Provisional application No. 63/151,629, filed on Feb. 19, 2021, provisional application No. 62/979,403, filed on Feb. 20, 2020.

(51) Int. Cl.
A61F 2/24 (2006.01)

(52) U.S. Cl.
CPC .......... A61F 2/2466 (2013.01); A61F 2/2451 (2013.01); A61F 2/2487 (2013.01)

(58) Field of Classification Search
CPC .... A61F 2/2466; A61F 2/2451; A61F 2/2409; A61M 2025/0681; A61M 2025/0024;
(Continued)

(56) References Cited

U.S. PATENT DOCUMENTS

2004/0193283 A1* 9/2004 Rioux ................... A61M 25/04
623/23.66
2012/0232574 A1 9/2012 Kim et al.
(Continued)

FOREIGN PATENT DOCUMENTS

CN        110234298 A       9/2019
JP        2006527629 A   * 12/2006   ........ A61M 25/0082
(Continued)

OTHER PUBLICATIONS

Translation of description for WO 2019/103540 (Year: 2019).*
(Continued)

*Primary Examiner* — Brian E Pellegrino
(74) *Attorney, Agent, or Firm* — Justin H. Kim

(57)        ABSTRACT

The present invention relates to a system and method for transcatheter treatment for tricuspid regurgitation. The system for transcatheter treatment for tricuspid regurgitation, according to one preferred embodiment of the present invention, includes: the coronary sinus tube inserted into the coronary sinus; and the tricuspid valve tube traversing the tricuspid valve, wherein the coronary sinus tube and the tricuspid valve tube communicate with each other or are adjacent to each other within a range of predetermined length at an upper side and are separate from each other at a lower side, and a blocking member for blocking a space generated by incomplete closing of the tricuspid valve is provided at a lower part of the tricuspid valve tube or between the coronary sinus tube and the tricuspid valve tube.

11 Claims, 27 Drawing Sheets

(58) Field of Classification Search
CPC ............ A61N 2001/0585; A61B 17/82; A61B
2090/033
USPC ...................................................... 623/1.27
See application file for complete search history.

(56) References Cited

U.S. PATENT DOCUMENTS

| | | |
|---|---|---|
| 2016/0038287 A1 | 2/2016 | Lederman et al. |
| 2016/0193043 A1 | 7/2016 | Kim |
| 2017/0119489 A1 | 5/2017 | Kim |
| 2017/0224488 A1 | 8/2017 | Lederman et al. |
| 2020/0015850 A1 | 1/2020 | Kim et al. |

FOREIGN PATENT DOCUMENTS

| | | | |
|---|---|---|---|
| JP | 2013537084 A | 9/2014 | |
| WO | WO-2019046205 A1 * | 3/2019 | ......... A61B 17/0467 |
| WO | 2019103540 | 5/2019 | |

OTHER PUBLICATIONS

Translation of JP2006527629 (Year: 2006).*
International Search Report dated May 5, 2021 from corresponding
International Application No. PCT/US2021/018942.
Office Action dated Apr. 19, 2025 from corresponding CN Application No. 202180015918.1.

* cited by examiner

Tricuspid valve (TV)

hole

15

12

12e hole

12

15

TRANSCATHETER SYSTEM AND METHOD FOR REDUCING TRICUSPID REGURGITATION

FIELD

The present invention relates to a system and method for reducing transcatheter treatment for tricuspid regurgitation and, more particularly, to the system and method for transcatheter treatment for reducing tricuspid regurgitation, wherein the system and method can perform a catheter treatment for reducing tricuspid regurgitation which is a heart disease where the tricuspid valve does not close completely, thereby causing the blood to flow backward in the heart.

BACKGROUND

A human heart is divided into four chambers: two atria and two ventricles, which are connected to four blood vessels such as the main artery, the main vein, the pulmonary artery and the pulmonary vein, thereby functioning as a passage for blood delivery. An interventricular septum in the center of the heart separates the heart into two sides: right atrium and right ventricle in one side, and left atrium and left ventricle in the other side. The tricuspid valve is located between the right atrium and the right ventricle, and the mitral valve is located between the left atrium and the left ventricle.

The heart functions as a pump by repeating contraction and relaxation, to allow the blood to flow along the blood vessels. In the systole of the heart, as the blood in the heart flows forwardly to the blood vessels, the blood in the right heart is delivered from the right ventricle to the pulmonary artery and the blood in the left heart is delivered from the left ventricle to the main artery.

However, if a valve between an atrium and a ventricle does not properly operate, the blood of the ventricle flows backward in the systole of the heart, that is, moves toward the atrium. If the tricuspid valve between the right atrium and the right ventricle does not properly operate, the blood of the right ventricle flows backward into the right atrium; this is called "tricuspid regurgitation", and if the mitral valve between the left atrium and the left ventricle does not property operate, the blood of the left ventricle flows backward into the left atrium. This is called "mitral regurgitation".

In tricuspid regurgitation, the blood is not delivered to the pulmonary artery when the heart contracts because the tricuspid valve does not properly operate, thus causing the blood to flow backward into the right ventricle. This is called "tricuspid insufficiency". An outbreak of tricuspid regurgitation is caused since the tricuspid valve does not close completely when it should close because the tricuspid valve between the right atrium and the right ventricle of the heart is stretched or torn, or the chordae tendinae to fix the valve between them is broken.

As typical treatments for the tricuspid regurgitation according to the conventional art, methods of correcting the disease surgically by opening a patient's chest and cutting the heart, that is, an annuloplasty ring method and a DeVega method, have been widely used. However, in these surgical methods, as a surgical treatment highly invasive should be performed, the surgical approach only for the tricuspid valve has not been widely used because the importance of the tricuspid valve is relatively low. That is, when a patient having tricuspid regurgitation underwent a mitral valve surgery or an important heart disease surgery of the coronary arteries, etc., the surgical treatment of the tricuspid regurgitation as described above was done simultaneously.

In this regard, there has been a gradually growing global expectation on research for treatment for tricuspid regurgitation, which may be performed using a catheter or a simple device, rather than a surgical method of opening the chest and cutting the heart.

SUMMARY

Cerclage Method: In one aspect, this invention is a method of treating tricuspid valve regurgitation in a patient. The method uses: (i) a cerclage filament, and (ii) a having a sleeve tube. The sleeve tube comprises a main segment, a coronary sinus leg, a tricuspid valve leg, and a spacer body mounted on the tricuspid valve leg. The method comprises making a vascular entry site into an entry vein. The entry vein could be any suitable vein in the patient's body, such as the subclavian vein or the femoral vein. The method further comprises inserting the cerclage filament through the vascular entry site and entry vein, and further into the patient's heart.

When fully inserted, the path taken by the cerclage filament is into the right atrium, through the coronary sinus, through the great cardiac vein, out into the right ventricle (as used herein 'right ventricle' includes the right ventricular outflow tract), through the tricuspid valve, back into the right atrium, back through the entry vein, and exit back out of the vascular entry site. The entry into the right ventricle may occur by perforating out of the interventricular septum, in particular, the membranous ventricular septum located at the right ventricular outflow tract. This path by the cerclage filament makes a cerclage loop. The path of the cerclage filament could also include entering a septal perforator vein before exiting out the septum and into the right ventricle.

The method further comprises sliding the sleeve tube onto the cerclage filament. Because the cerclage filament makes a loop, the cerclage filament can be considered as having an entry segment (directed towards the heart) and a return segment (directed away from the heart). In some embodiments, the step of sliding the sleeve tube onto the cerclage filament comprises: (i) sliding the coronary sinus leg over one of the entry segment or the return segment of the cerclage filament; (ii) sliding the tricuspid valve leg over the other of the entry segment or the return segment of the cerclage filament. For example, the entry segment of the cerclage filament could be slid onto the coronary sinus leg and the return segment of the cerclage filament could be slid onto the tricuspid valve leg. This would be compatible with the path and orientation taken by the cerclage filament through the heart. However, the opposite configuration is also possible.

The method further comprises advancing the sleeve tube towards the patient's right atrium. The sleeve tube may pass through the superior or inferior vena cava on its way into the right atrium. The sleeve tube is advanced so that the coronary sinus leg goes into the patient's coronary sinus in the right atrium and the tricuspid valve leg goes through the patient's tricuspid valve. The sleeve tube or cerclage filament is manipulated to position the spacer body between the leaflets of the patient's tricuspid valve. This step of positioning the spacer body could be performed while monitoring with an echocardiogram. The purpose of the spacer body is to provide a good surface for improved coaptation of the valve leaflets.

With the cerclage loop having been created, the method further comprises locking the cerclage loop by fastening together a portion of the entry segment of the cerclage filament to an opposing return segment of the cerclage filament. This fastening together could occur at any suitable place in the patient's body at a location outside the right atrium. For example, in the situation where the entry vein is a femoral vein, this fastening together could occur at a location in the inferior vena cava that is superior to one or both the renal veins of the patient. Likewise, in this situation, the proximal end of the sleeve tube could terminate at a location in the inferior vena cava that is superior to one or both renal veins. The method may further comprise anchoring the cerclage loop at an anchoring site in the patient's body. For example, in the situation where the entry vein is a subclavian vein, this anchoring could occur at a subcutaneous pocket near (within 10 cm) the subclavian vein entry site.

In some embodiments, the sleeve tube further comprises a stopper located at the distal end of the tricuspid valve leg. In this situation, the method further comprises positioning the stopper against a wall of the right ventricle of the patient. The purpose of the stopper is to abut against the right ventricle wall where the cerclage filament perforates out. Thus, the stopper prevents the tricuspid valve leg of the sleeve tube from becoming embedded into the ventricle wall.

The path for the cerclage filament could be created using a guidewire. In this embodiment, the method comprises inserting the guidewire through the vascular entry site and advancing the guidewire into the right atrium of the patient. The guidewire may travel through the superior or inferior vena cava on its way into the right atrium. The distal end of the guidewire is inserted into the coronary sinus. The guidewire is advanced through the heart and its distal end is made to enter the right ventricle of the patient.

In some embodiments, an introducer sheath is slid over the guidewire, and contrast agent injected through the sheath to perform a coronary venogram. This allows identifying a septal perforator vein and advancing the guidewire into the septal perforator vein. The guidewire follows a path that enters into the right ventricle. This could be performed by advancing the guidewire to perforate out of the interventricular septum, in particular, the membranous ventricular septum located at the right ventricular outflow tract. The guidewire is grasped (e.g. in the right ventricle with a snare catheter) and its distal end pulled out of the entry vein.

The guidewire is exchanged with the cerclage filament such that the cerclage filament takes the path through the patient's heart. In some embodiments, this guidewire exchange involves inserting an introducer sheath over the guidewire, then withdrawing the guidewire, and advancing the cerclage filament through the introducer sheath. In some embodiments, this guidewire exchange involves attaching the distal end of the cerclage filament to the proximal end of the guidewire and pulling the guidewire out such that the cerclage filament follows the path created by the guidewire.

In some embodiments, there may be an overpass arch on the cerclage filament and the method further comprises positioning the overpass arch inside the great cardiac vein at a position over a coronary artery. The purpose of the overpass arch is to avoid compressing the coronary artery passing underneath. Thus, the path taken by the cerclage filament could arch over the coronary artery as the cerclage filament passes through the great cardiac vein. The above-described method of this invention aspect could be performed using the heart cerclage assembly or the heart cerclage kit as described below.

Heart Cerclage Assembly: In another aspect, this invention is a heart cerclage assembly comprising: (i) a cerclage filament, and (ii) a sleeve tube through which the cerclage filament travels. The cerclage filament may be defined as a wire, rope, cord, string, or any other type of thin highly flexible thread-like line. The cerclage filament may be of any suitable thickness. In some embodiments, the cerclage filament has a thickness in the range of 0.3-1.0 mm. An example of a cerclage filament is a nylon-coated, braided stainless steel wire. Cerclage filament has various different segments. Among them, the cerclage filament has an entry segment and a return segment.

The sleeve tube comprises: (a) a main segment; (b) a coronary sinus leg; (c) a tricuspid valve leg; and (d) a spacer body mounted on the tricuspid valve leg. The sleeve tube may be made of any suitable material or combination of materials, such as metal or plastic materials. Various components of the sleeve tube may be made of the same or different materials. The segments of the sleeve tube have different lengths. The tricuspid valve leg is longer than the coronary sinus leg. The main segment is longer than the tricuspid valve leg and longer than the coronary sinus leg. A juncture is defined at the point on the sleeve tube where the two legs separate out from the main segment.

In some embodiments, the main segment of the sleeve tube has a length in the range of 25-65 cm; and in some cases, in the range of 30-55 cm; and in some cases, about 45 cm. This may be useful in situations where the entry vein is a subclavian vein and positioning of the cerclage assembly as explained above. In some embodiments, the main segment of the sleeve tube has a length in the range of 6-20 cm; and in some cases, in the range of 8-18 cm. This may be useful in situations where the entry vein is a femoral vein and positioning of the cerclage assembly as explained above. In some embodiments, the tricuspid valve leg has a length in the range of 4.0-11 cm; and in some cases, in the range of 5.5-9.0 cm. In some embodiments, the coronary sinus leg has a length in the range of 2.2-5.0 cm; and in some cases, about 3.0 cm.

The heart cerclage assembly is assembled such that both the entry segment and the return segment of the cerclage filament travel through the main segment of the sleeve tube. Furthermore, one of the entry segment or the return segment travels through the coronary sinus leg of the sleeve tube. And the other of the entry segment or the return segment travels through the tricuspid valve leg of the sleeve tube. For example, the entry segment could travel through the coronary sinus leg and the return segment could travel through the tricuspid valve leg; or vice versa.

The main segment of the sleeve tube may be single-barreled or double-barreled with two conjoined barrels. In the single-barreled design, both the entry segment and the return segment travel through the single barrel of the main segment before separating at the two legs. In the double-barreled design, the entry segment travels through one of the two barrels, and the return segment travels through the other of the two barrels. The two barrels are separately contiguous with the tricuspid valve leg and coronary sinus leg, respectively.

The tricuspid valve leg may have a telescoping feature. In such embodiments, the tricuspid valve leg can be extended and retracted. As such, the tricuspid valve leg could have a retracted length and an extended length. Any suitable mechanism may be implemented for providing this telescoping feature. For example, tricuspid valve leg could comprise an inner and outer tube that slide against each other.

The sleeve tube further comprises a spacer body mounted on the tricuspid valve leg. The spacer body can have any suitable shape, such as cylindrical, crescent, spherical, ellipsoid, ovoid, wing, etc. In some embodiments, the spacer body has a curved croissant-shape. The spacer body can have any suitable structure, such as balloon (e.g. foam or air-filled), basket, mesh, struts (e.g. like a stent), framework, skeleton, scaffolding, blocking device, etc. If needed, a surface for the spacer body may be provided in any suitable manner, such as a skin, shell, casing, or membrane. The spacer body may be made of any suitable material, such as plastics, metals, or combinations thereof.

The spacer body is made to have dimensions suitable for providing a coaptation surface for leaflets of the tricuspid valve. In some embodiments, the spacer body has a length in the range of 20-60 mm; and in some cases, in the range of 30-50 mm. As used herein, 'length' for the spacer body means its length as measured along the tricuspid valve leg of the tube. The spacer body may have a relaxed and elongated configuration. In this situation, the measurements above for the spacer body are made in the relaxed configuration.

The width of the spacer body can be measured on a cross-section plane that is orthogonal to the longitudinal axis. On this cross-section plane, there is a wide axis for which the spacer body has its widest width, and a cross-axis that is orthogonal to that wide axis. In some embodiments, the width of the spacer body on the wide axis is in the range of 7-30 mm; and in some cases, in the range of 10-25 mm. In some embodiments, width of the spacer body on the cross-axis is in the range of 7-30 mm; and in some cases, in the range of 10-25 mm. In some embodiments, the width of the spacer body on the wide axis is greater than the width of the spacer body on the cross-axis (i.e. non-circular cross-section). The spacer body may have a relaxed and elongated configuration. In this situation, the measurements above for the spacer body are made in the relaxed configuration.

In some embodiments, the cerclage assembly further comprises an overpass arch mounted on the cerclage filament. The overpass arch is a curve-shaped narrow tube through which the cerclage filament passes. The overpass arch could be made of any suitable rigid material, such as stainless steel or nitinol alloy. The overpass arch could have any suitable dimension for holding the cerclage filament and providing passage of the coronary artery. For example, the overpass arch could have an arch-to-base height of 2-6 mm and a length of 6-17 mm. In some embodiments, the sleeve tube further comprises a stopper located at the distal end of the tricuspid valve leg. The stopper is wider or has a greater diameter than the distal end of the tricuspid valve leg. Furthermore, the stopper has a width or diameter in the range of 2-6 mm.

In some embodiments, the cerclage assembly further comprises a lock that fastens together the entry segment of the cerclage filament to an opposing return segment. This lock could be located at the proximal end of the main segment of the sleeve tube. The heart cerclage assembly of this invention aspect may be assembled from the heart cerclage kit as described below.

Heart Cerclage Kit: In another aspect, this invention is a heart cerclage kit for treating tricuspid valve regurgitation in a patient. This heart cerclage kit could be used to make the heart cerclage assembly as described above. The heart cerclage kit comprises: (i) a cerclage filament; and (ii) a sleeve tube. The sleeve tube comprises: (a) a main segment;

(b) a coronary sinus leg; (c) a tricuspid valve leg; and (d) a spacer body located on the tricuspid valve leg.

The kit could further comprise a guidewire used to create a pathway for cerclage filament. The kit could further comprise an introducer sheath sliding over the guidewire, or exchanging out the guidewire with the cerclage filament, or providing a channel path for introducing the sleeve tube. The kit could further comprise a torque-applying tool for applying rotational torque to the guidewire. This may be particularly useful for twisting the guidewire to puncture through the septum wall. The kit could further comprise a lock for fastening together opposing segments of the cerclage filament together so that the cerclage loop is formed.

Additional Embodiments: The descriptions and examples given herein are intended merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

BRIEF DESCRIPTION OF THE DRAWINGS

Features and advantages of the claimed subject matter will be apparent from the following description of embodiments consistent therewith, which description should be considered in conjunction with the accompanying drawings, wherein:

DESCRIPTION

Figure 1A:
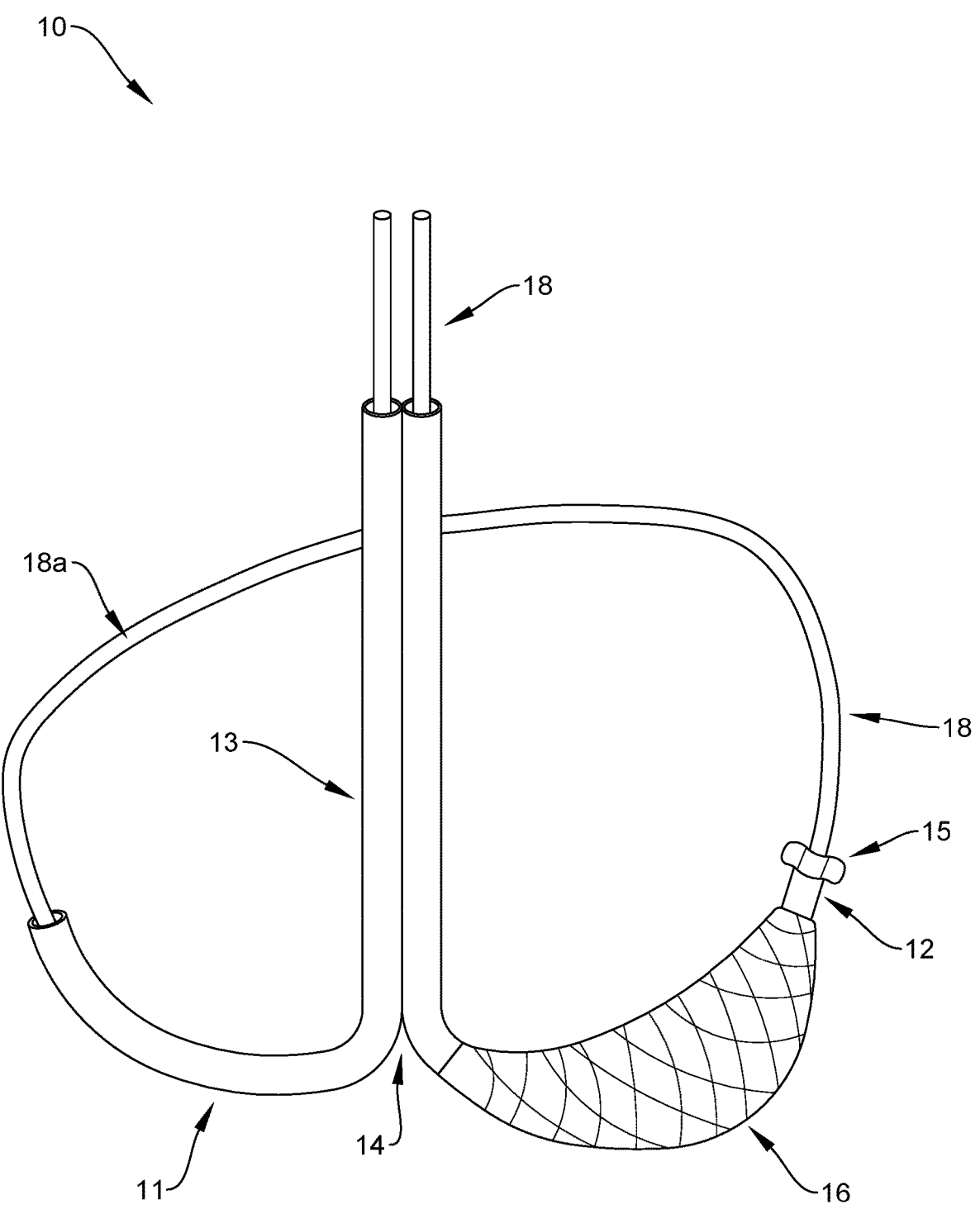
FIG. 1A depicts an embodiment of the transcatheter system which includes a longitudinal stem portion consistent with the present disclosures.

To assist in understanding the invention, reference is made to the accompanying drawings to show by way of illustration specific embodiments in which the invention may be practiced. The drawings herein are not necessarily made to scale or actual proportions. For example, lengths and widths of the components may be adjusted to accommodate the page size.

A transcatheter system 10 on a cerclage filament 18 for treating regurgitation in a cardiac tricuspid valve of a heart may include a first catheter tube 12 having a peripheral outer surface and a distal end and defining an axis. The first catheter tube 12 may be dimensioned to extend through the tricuspid valve. The transcatheter system 10 may further include a spacer body 16 provided proximate the distal end of the first catheter tube 12 projecting from the peripheral outer surface. The spacer body 16 may be dimensioned to intersect a space in the tricuspid valve generated by incomplete closure thereof.

The spacer body 16 may be configured to intersect, at an oblique angle with respect to the axis, a space in the tricuspid valve generated by incomplete closure thereof. The spacer body 16 may include an expandable stent and a membrane portion defined between the outer peripheral edge and the peripheral outer surface of the first catheter tube 12. At least one of a size or a shape of the spacer body 16 may be adjustable in volume.

The transcatheter system 10 may further include a stopper 15 defined on the first catheter tube 12 configured to prevent the distal end from piercing an intraventricular septum of the heart.

One embodiment of the transcatheter system 10 on a cerclage filament 18 for treating regurgitation in a cardiac tricuspid valve in a heart may include a first catheter tube 12 having a first peripheral outer surface and a distal end and defining an axis. The first catheter tube 12 may be dimensioned to extend through the tricuspid valve. The transcatheter system 10 may further include a spacer body 16 provided proximate the distal end of the first catheter tube 12 projecting from the peripheral outer surface, the spacer body 16 being dimensioned to intersect a space in the tricuspid valve generated by incomplete closure thereof.

The transcatheter system 10 may further a second catheter tube 11 having a second outer peripheral surface provided in contact with the first outer peripheral surface for a selected distance and branching away from the first outer peripheral surface at a selected position spaced away from the distal end of the first catheter tube 12.

The spacer body 16 may be configured to intersect, at an oblique angle with respect to the axis, a space in the tricuspid valve generated by incomplete closure thereof. The second catheter tube 11 may be configured to enter a coronary sinus of the heart. At least one of a size, a shape, or a position of the spacer body 16 may be adjustable.

The transcatheter system 10 may further include a stopper 15 defined on the first catheter tube 12 configured to prevent the distal end from piercing an intraventricular septum of the heart. The transcatheter system 10 may further include an overpass arch 18a defined intermediate the distal end of the first catheter tube 12 and a distal end of the second catheter tube 11 configured to overpass a coronary artery of the heart.

FIG. 1A depicts one embodiment of a transcatheter system 10. The transcatheter system 10 may include a main segment 13, a stopper 15 and a spacer body 16. The main segment 13 may separate into a coronary sinus leg 11 and a tricuspid valve leg 12. A juncture 14 may be defined as where the main segment 13 separate into the coronary sinus leg 11 and a tricuspid valve leg 12.

As shown in FIG. 1A and FIGS. 20-24, the coronary sinus leg 11 may be configured to wrap around or encircle the mitral valve (MV) through the coronary sinus (CS), and the tricuspid valve leg 12 may be configured to traverse or extend through the orifice of tricuspid leaflets. A stopper 15 may be disposed at the distal end of the tricuspid valve leg 12 so that the stopper 15 prevents the distal end from advancing further into the interventricular septum (IVS) as illustrated in FIGS. 20-24. The juncture portion 14 may be placed at or near the orifice of the coronary sinus. The tricuspid valve leg 12 may be configured to be suspended freely in a reverse "C" shape through the orifice of the tricuspid leaflets. The tricuspid valve leg 12 may be rigid enough to resist being bent as tension is applied onto the cerclage filament 18 or cerclage filament 19. The spacer body 16 may be attached onto the tricuspid valve leg 12 between the juncture portion 14 and the stopper 15.

Figure 1B:
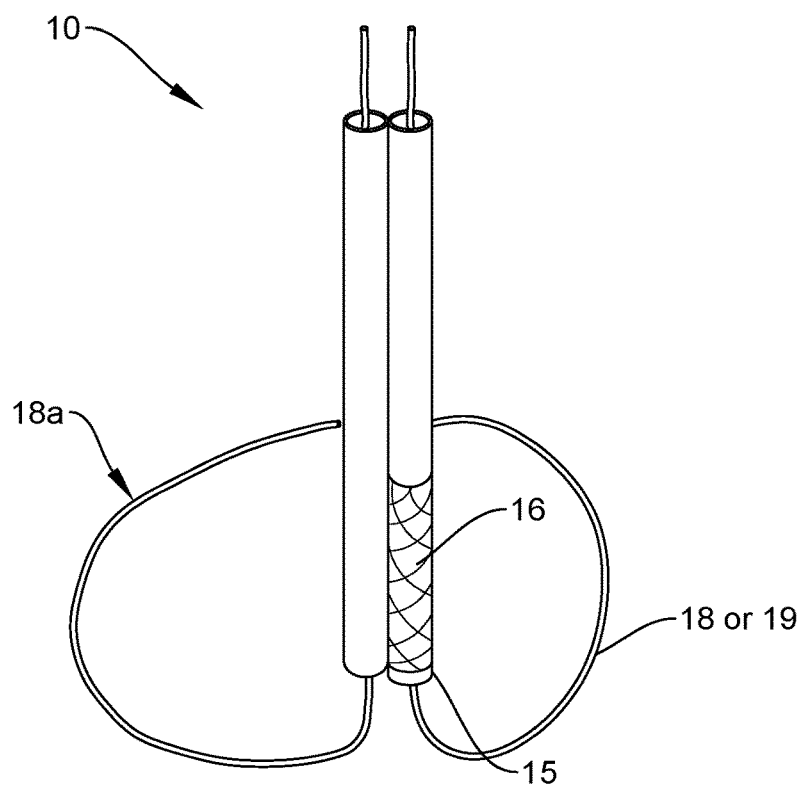
FIG. 1B depicts the transcatheter system which is inserted over the cerclage filament consistent with the present disclosure.
Figure 1C:
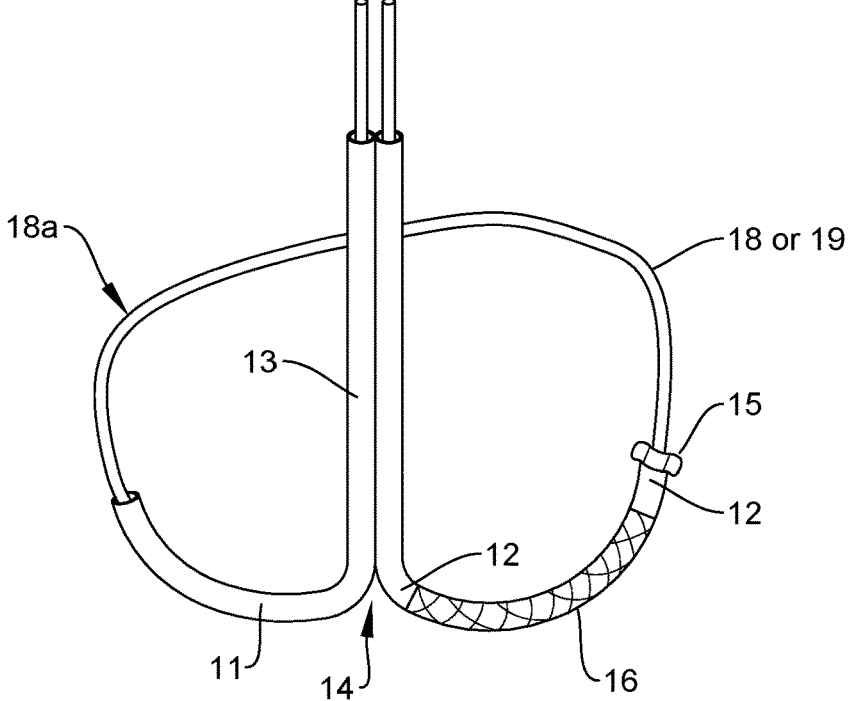
FIG. 1C depicts the transcatheter system when a tricuspid valve leg and a coronary sinus leg are expanded consistent with the present disclosure.

As shown in FIG. 1B and FIG. 1C, once the cerclage filament 18 is in place, the transcatheter system 10 may be inserted over the cerclage filament 18 thus positioned within the heart. The cerclage filament 18 may include an arch part 18a. The arch part 18a may be configured to overpass the coronary artery when tension is applied.

Figure 2:
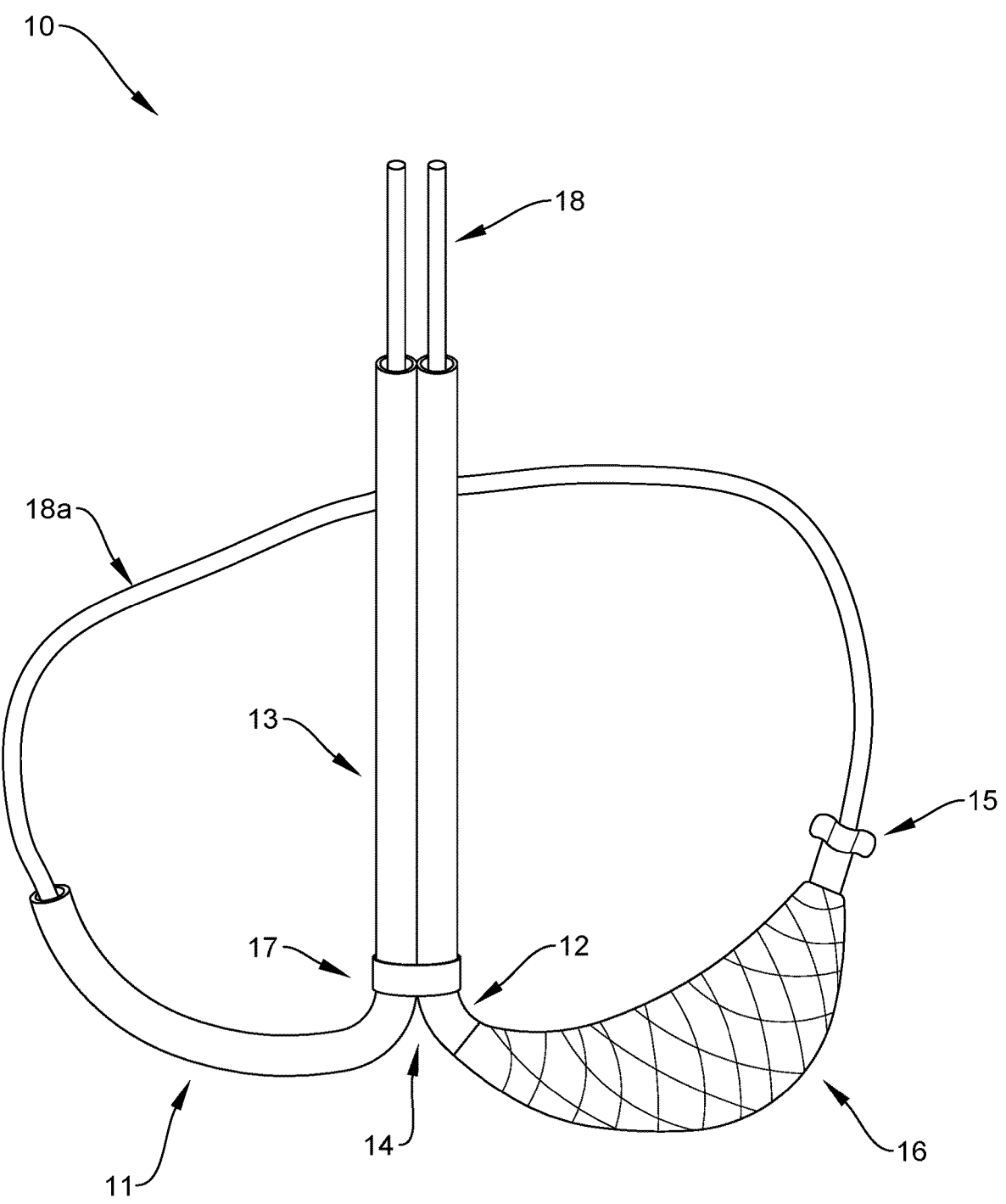
FIG. 2 depicts the transcatheter system which includes a hinge ring consistent with the present disclosure.

According to one aspect as shown in FIG. 2, the transcatheter system 10 may also include a hinge ring 17 around the juncture portion 14. The hinge ring 17 may be configured to reinforce the juncture portion 14 from being separated from the tension.

Figure 3:
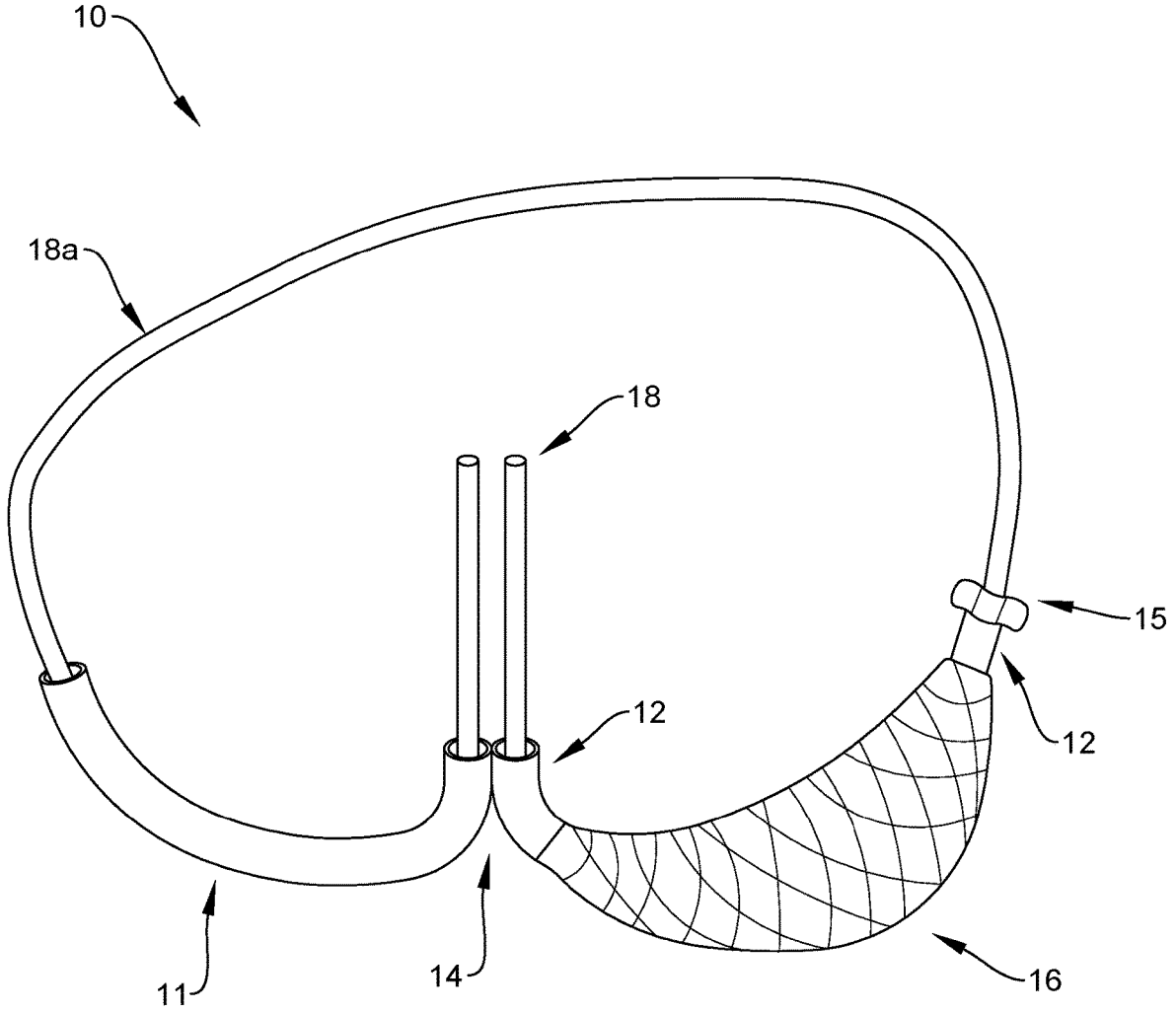
FIG. 3 depicts the stemless transcatheter system consistent with the present disclosure.
Figure 4:
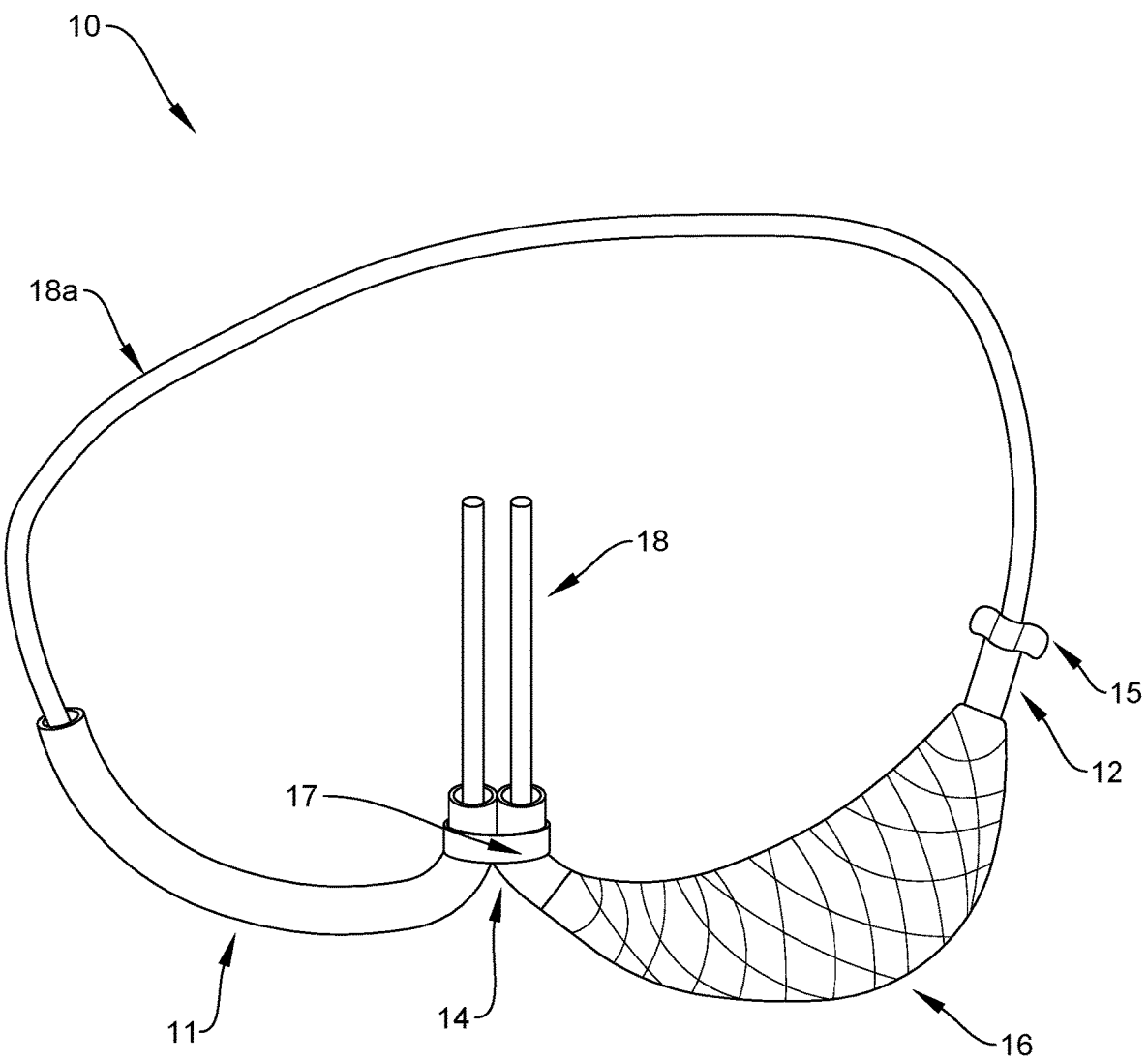
FIG. 4 depicts the stemless transcatheter system that include a hinge ring consistent with the present disclosure.

FIG. 3 shows an embodiment of a stemless transcatheter system 10 where it is configured without the stem portion 13. FIG. 4 shows the stemless transcatheter system 10 with the hinge ring 17 added for reinforcement.

Figure 5:
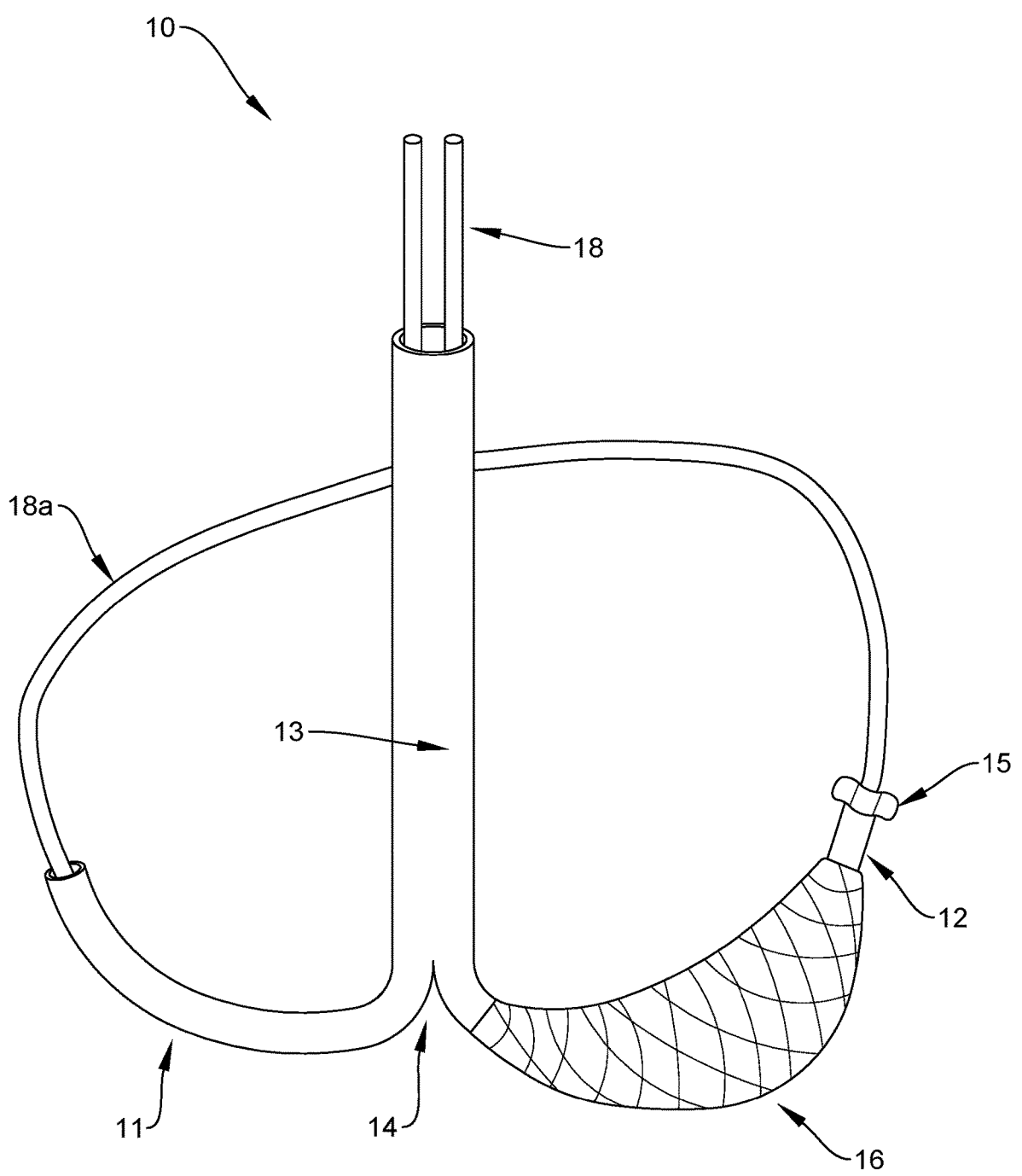
FIG. 5 depicts the one-tube stem transcatheter system consistent with the present disclosure.
Figure 6:
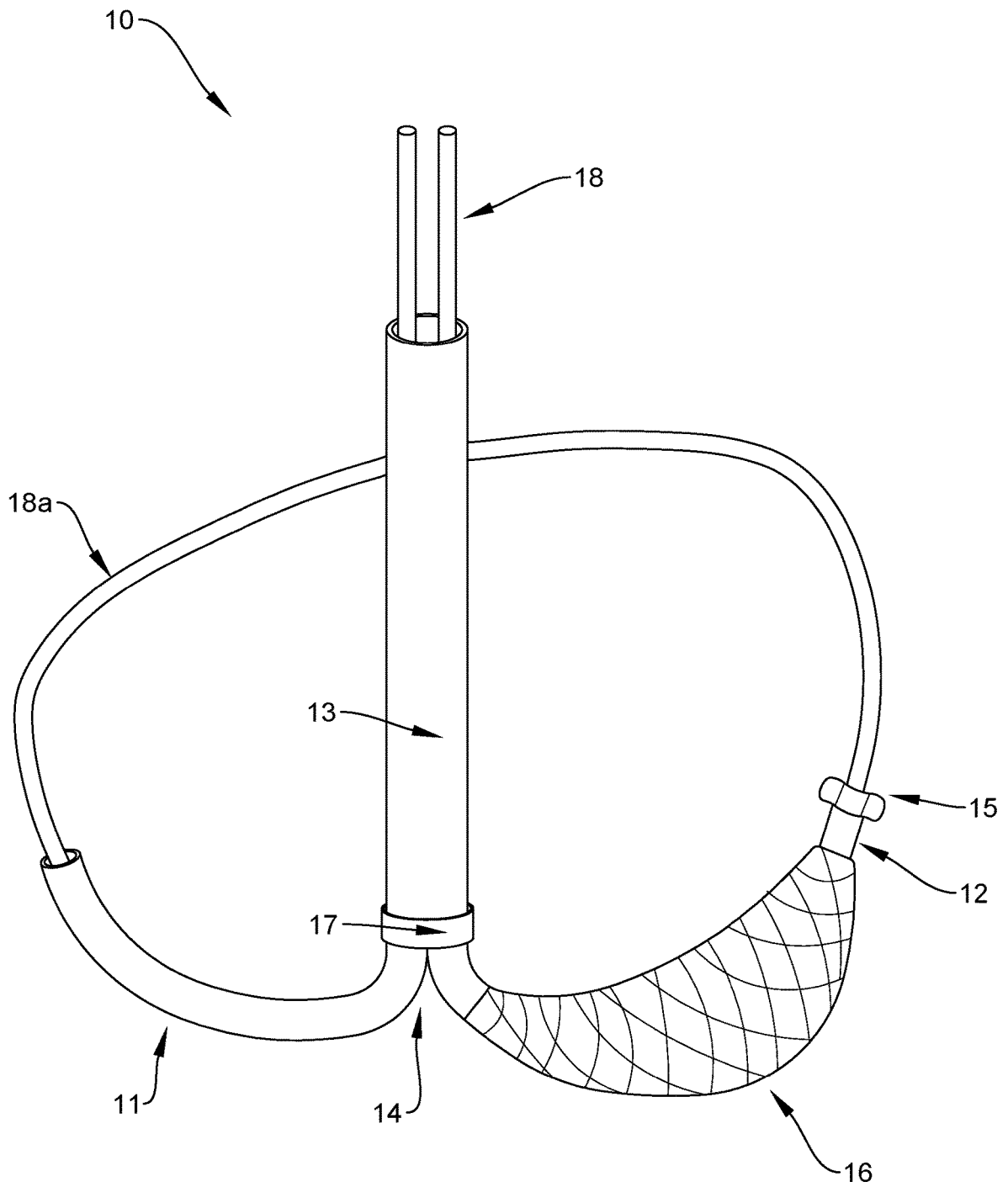
FIG. 6 depicts the one-tube stem transcatheter system with the hinge ring consistent with the present disclosure.

FIG. 5 shows an embodiment of one-tube stem transcatheter system 10 where the stem portion 13 may be configured as one main tube. The transcatheter system 10 then may separate at the hinge portion 14 into two tubes, the coronary sinus leg 11 and the tricuspid valve leg 12. FIG. 6 shows an embodiment of the one-tube stem transcatheter system 10 with the hinge ring 17 at the hinge portion 14.

Figure 7:
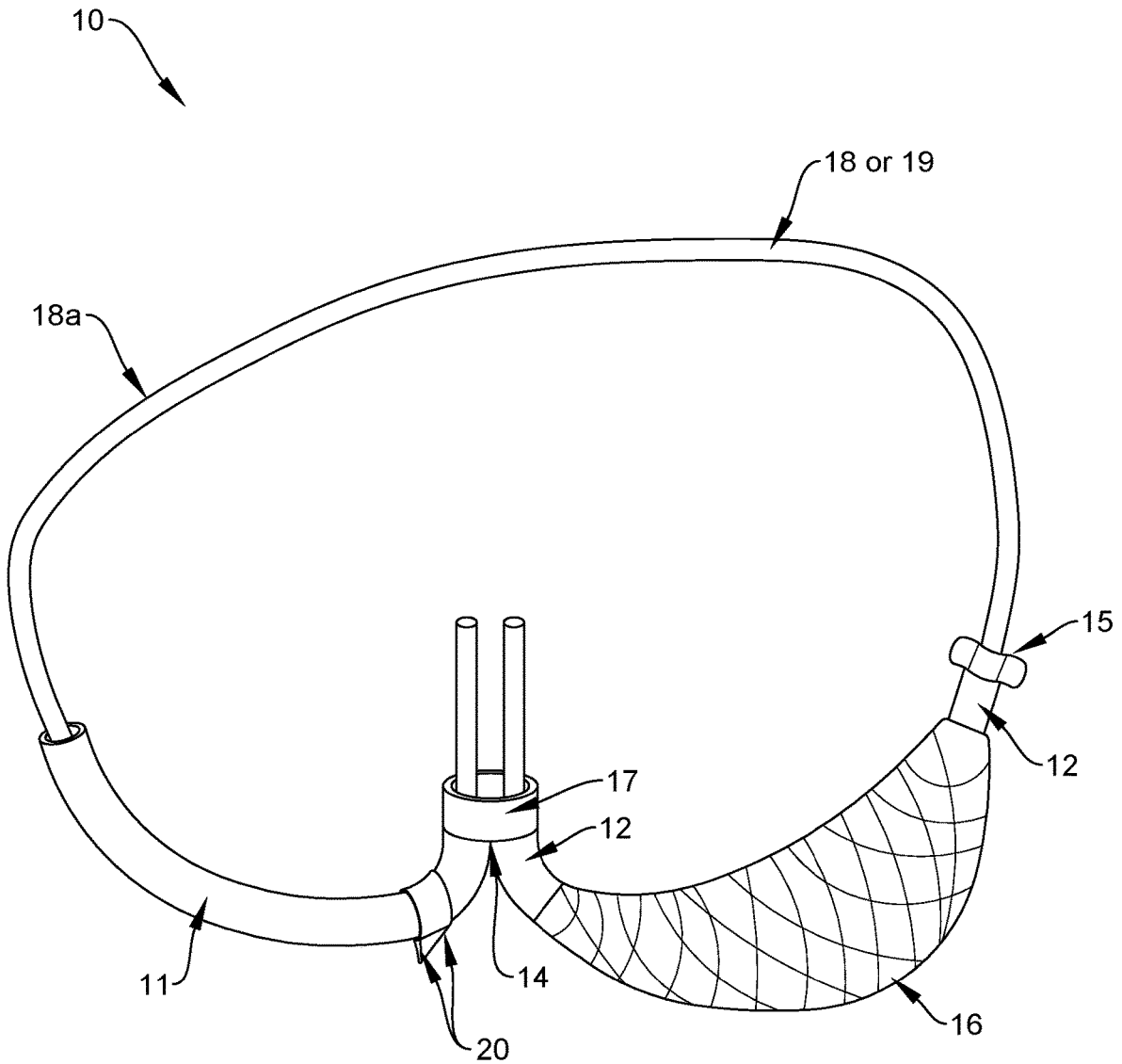
FIG. 7 depicts the one-tube stemless transcatheter system consistent with the present disclosure.

FIG. 7 shows an embodiment of one-tube stemless transcatheter system 10 that may separate at the juncture portion 14 into the coronary sinus leg 11 and the tricuspid valve leg 12. The one-tube stemless transcatheter system 10 may also include at least one anchor ring 20 place on the coronary sinus leg 11 and/or the tricuspid valve leg 12. The anchor ring(s) may be added on any embodiments of the transcatheter system 10.

Figure 8A:
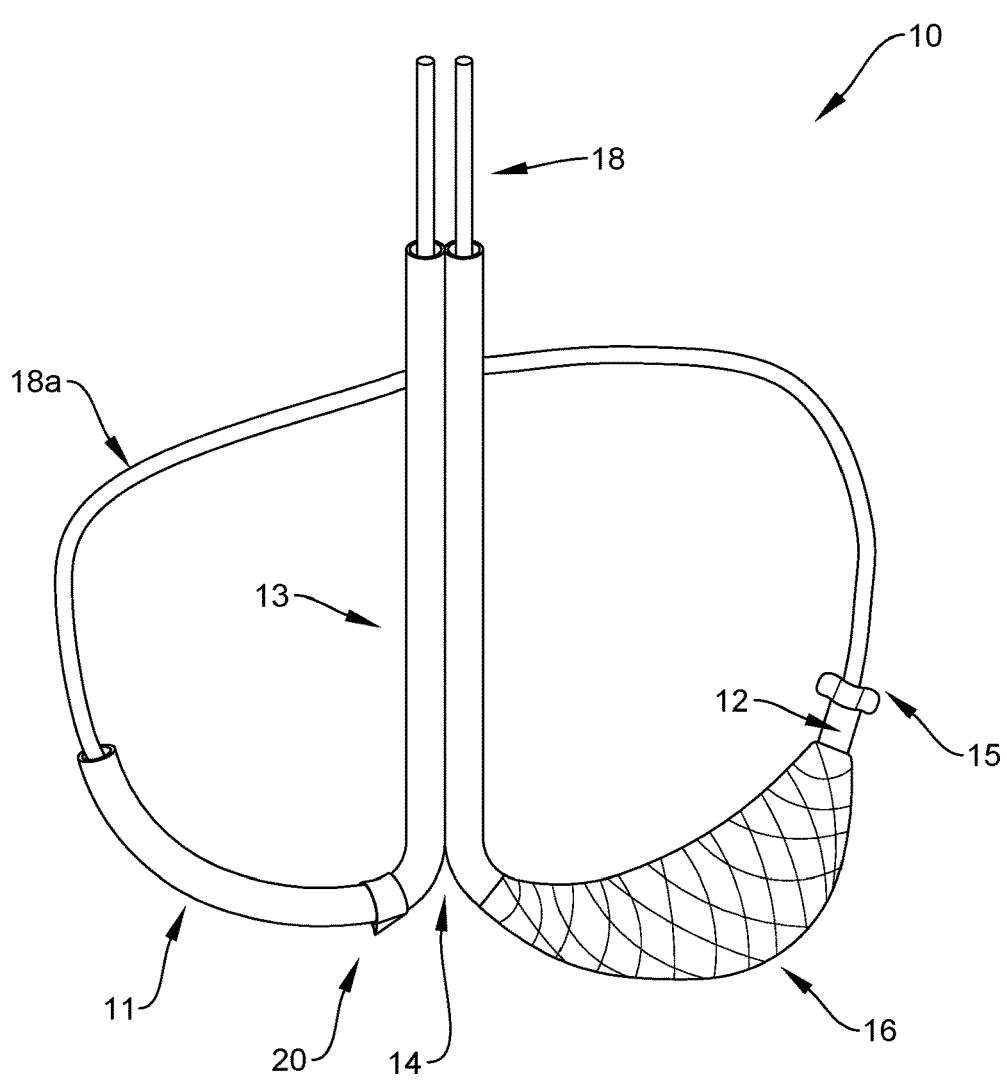
FIG. 8A depicts the transcatheter system which includes an anchor ring consistent with the present disclosure.
Figure 8B:
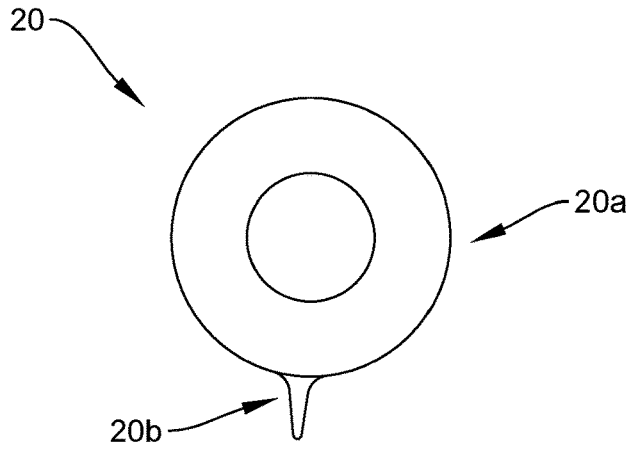
FIG. 8B depicts the anchor ring which include a ring body and an anchor consistent with the present disclosure.

As shown in FIGS. 8A-B, the transcatheter system 10 with at least one ring-shape anchor 20 placed on the coronary sinus leg 11. The ring-shaped anchor 20 may include a ring-body 20a and at least one anchor 21b. The anchor 20 may be configured to stabilize the transcatheter system 10 and to keep the juncture portion 14 in place throughout the heart's contractions.

Figure 9A:
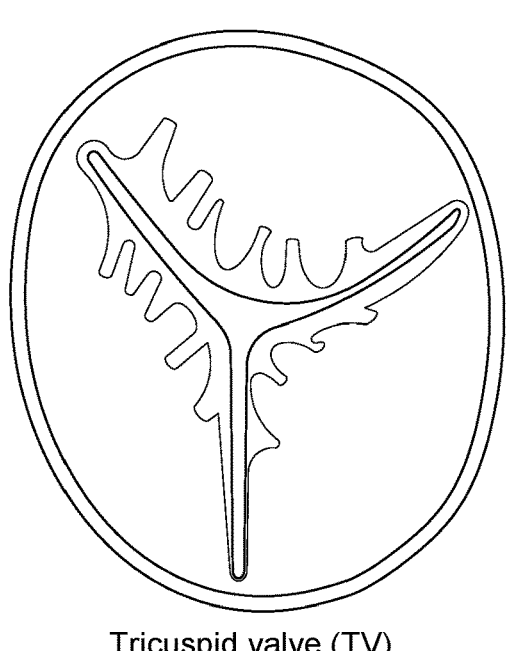
FIG. 9A depicts a diseased tricuspid valve consistent with the present disclosure.
Figure 9B:
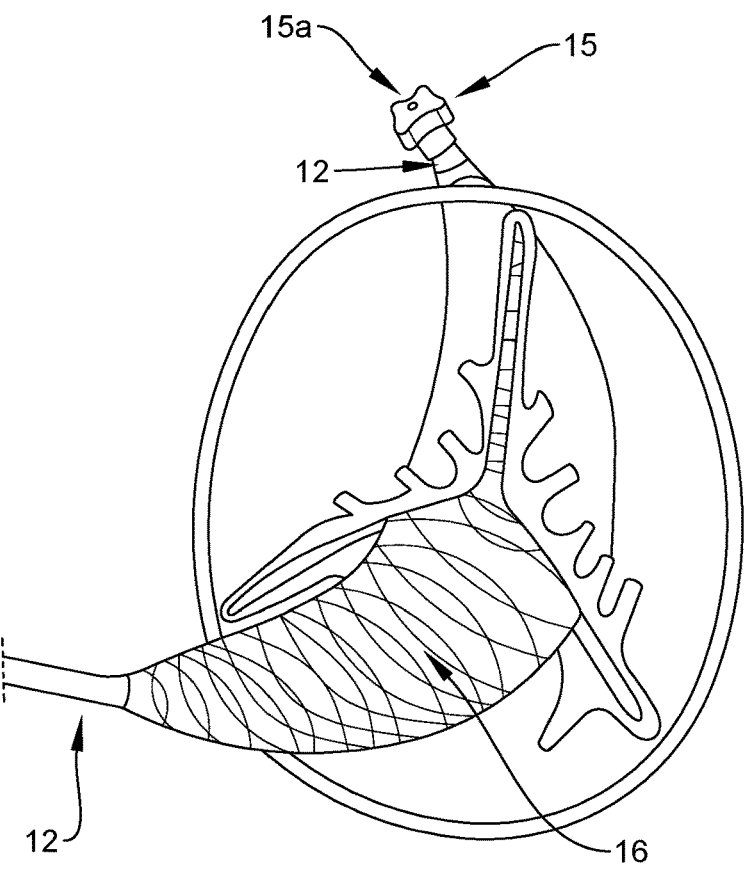
FIG. 9B depicts the spacer body placed through the diseased tricuspid valve consistent with the present disclosure.

FIG. 9A shows a diseased tricuspid valve with an orifice created due to an incomplete closure by its three leaflets resulting in tricuspid regurgitation. FIG. 9B shows the spacer body 16 placed through the orifice of the diseased tricuspid valve thus inducing coaptation of the tricuspid leaflets onto the spacer body 16 thereby reducing the incomplete closure and its regurgitation.

Figure 10A:
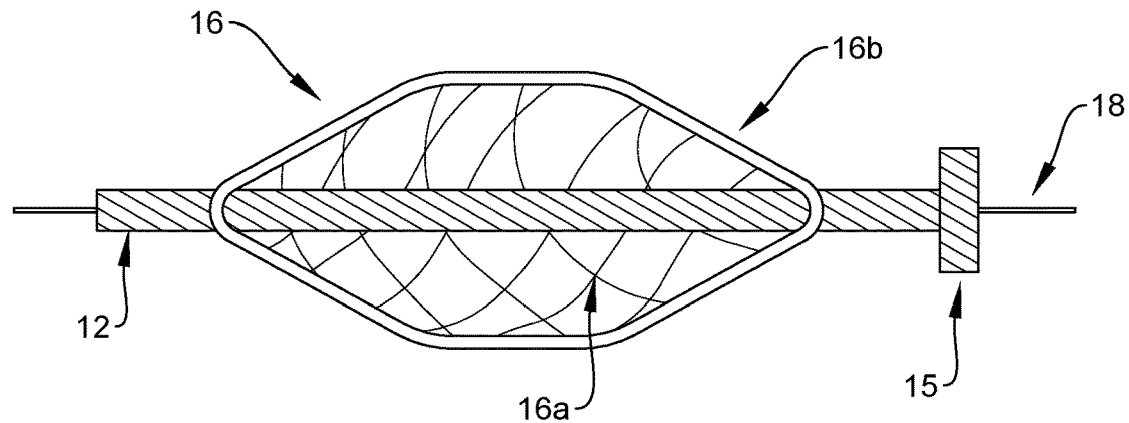
FIG. 10A depicts a side view of the spacer body when expanded, consistent with the present disclosure.
Figure 10B:
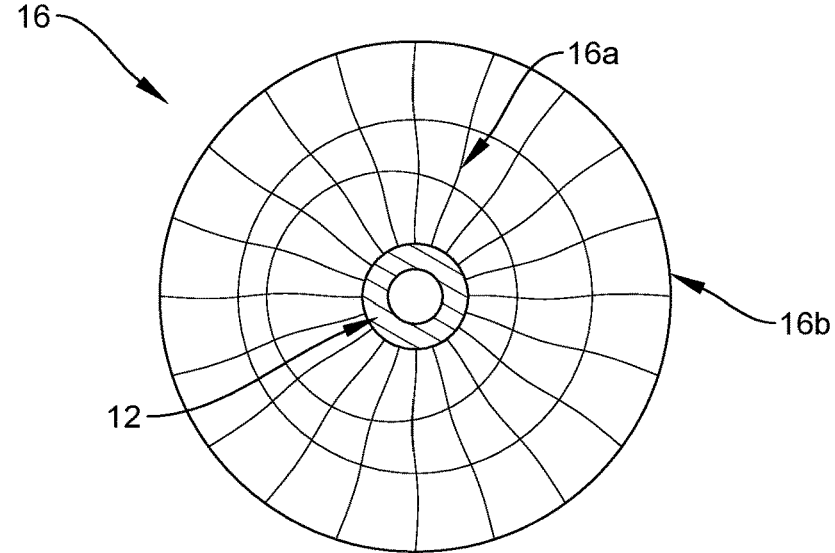
FIG. 10B depicts a cross-sectional view of the spacer body, consistent with the present disclosure.
Figure 10C:
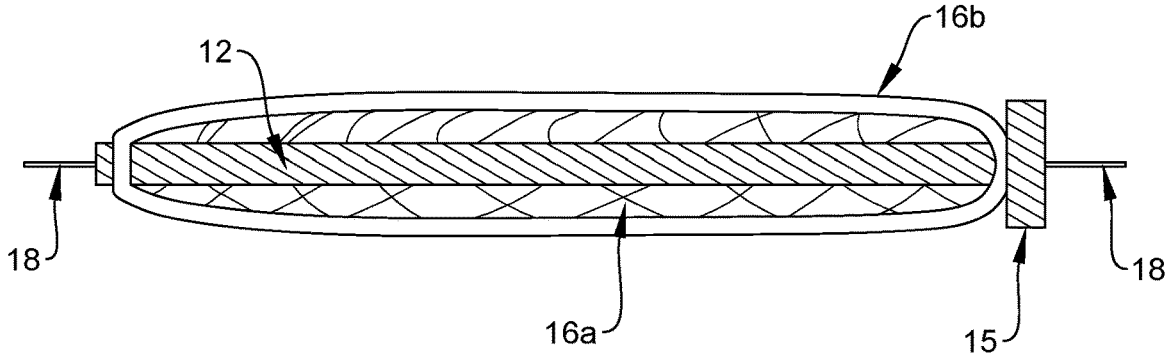
FIG. 10C depicts a side view of the spacer body when contracted, consistent with the present disclosure.

FIGS. 10A-C show one embodiment of the spacer body 16 which may include a stent 16a and at least one membrane 16b. The stent 16a may be expandable. The membrane 16a may be configured to cover the stent 16a entirely or partially. The stent 16a may be configured to be covered either inside or outside or both with the membrane 16b. The membrane 16b may be flexible and is made of flexible material such that the membrane 16b may be configured to expand or contract according to the movement of the stent 16a.

As illustrated in FIG. 10A, the spacer body 16 may be configured to be coaxially attached on along the longitudinal axis of the tricuspid valve leg 12. Both ends of the spacer body 16 may have a tapered shape. Those skilled in the art will recognize that the spacer body 16 may have a shape other than the tapered shape. FIG. 10B shows a cross-sectional view of the spacer body 16. FIG. 10C shows the spacer body 16 in its contracted state. The distal portion of the spacer body 16 may be configured to slide as it is expanded or contracted while the proximal portion may be fixed, or vice versa. Both ends of the spacer body 16 may also be configured to slide with expansion and contraction of the spacer body 16.

Figure 11A:
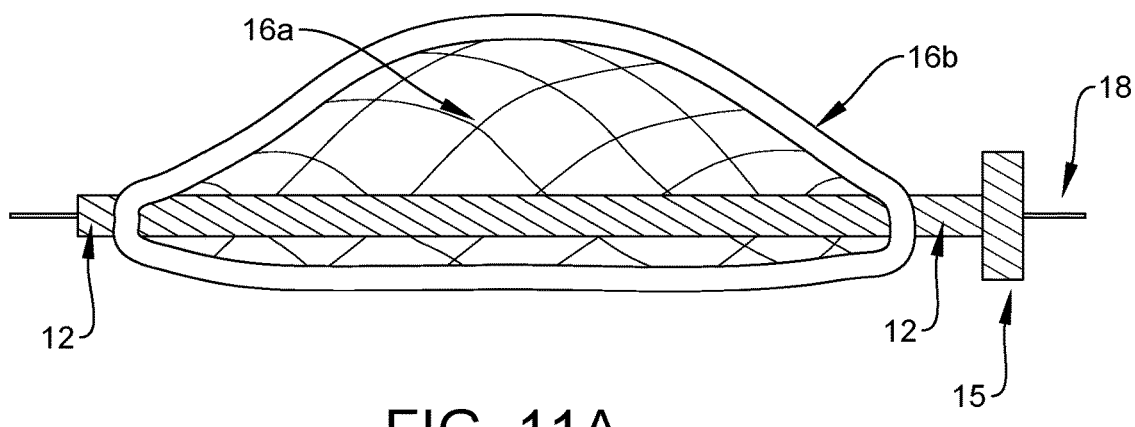
FIG. 11A depicts a side view of the spacer body when expanded, consistent with the present disclosure.
Figure 11B:
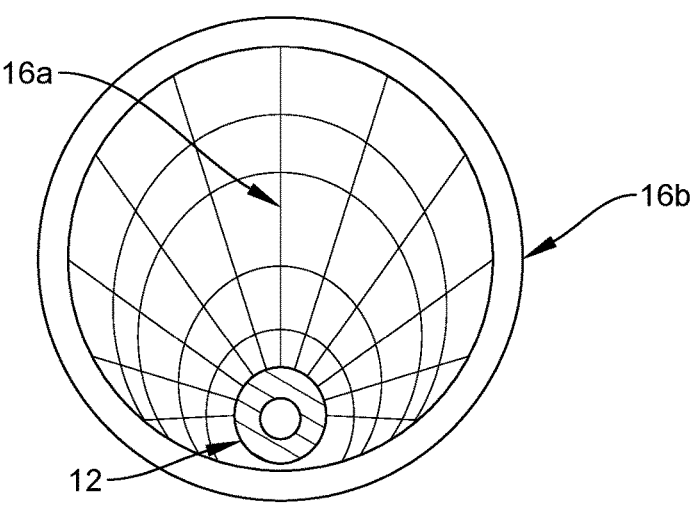
FIG. 11B depicts a cross-sectional view of the spacer body consistent with the present disclosure.
Figure 11C:
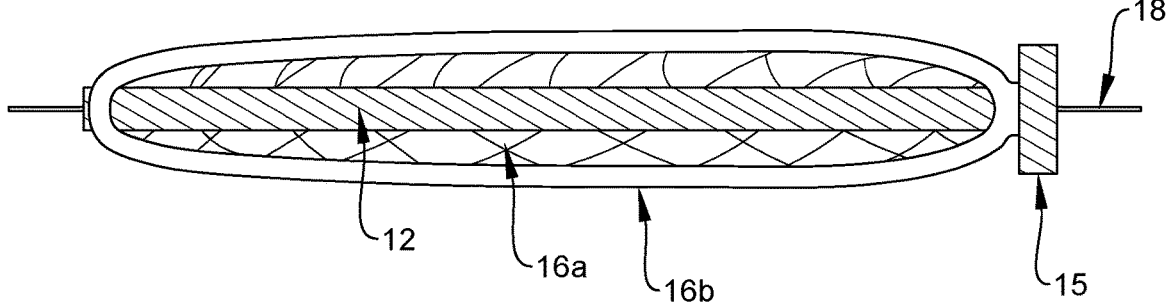
FIG. 11C depicts a side view of the spacer body when contracted, consistent with the present disclosure.

According to one aspect, FIGS. 11A-B shows the spacer body 16 in a croissant or crescent shape where the upper portion of the spacer body 16 may expand more than the bottom portion. FIG. 11B shows a cross-sectional view of the expanded spacer body 16, the tricuspid valve leg 12, and the cerclage filament 18. The spacer body 16 may be configured so that if the tricuspid valve leg bends or curves in reverse C-shape, the spacer body 16 may continue to maintain its croissant or crescent shape. Those skilled in the art will recognize that the spacer body 16 may have a shape other than the croissant or crescent. For example, the spacer body 16 may form an egg-shape or ball. FIG. 11C shows the spacer body 16 in its contracted state.

Figure 12A:
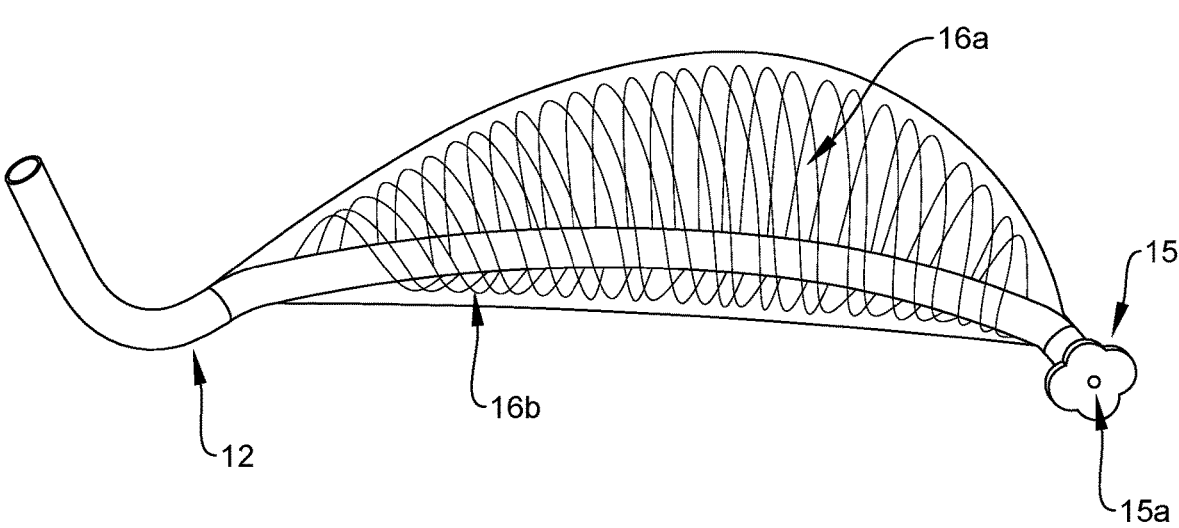
FIG. 12A is a perspective view of the spacer body when expanded, consistent with the present disclosure.
Figure 12B:
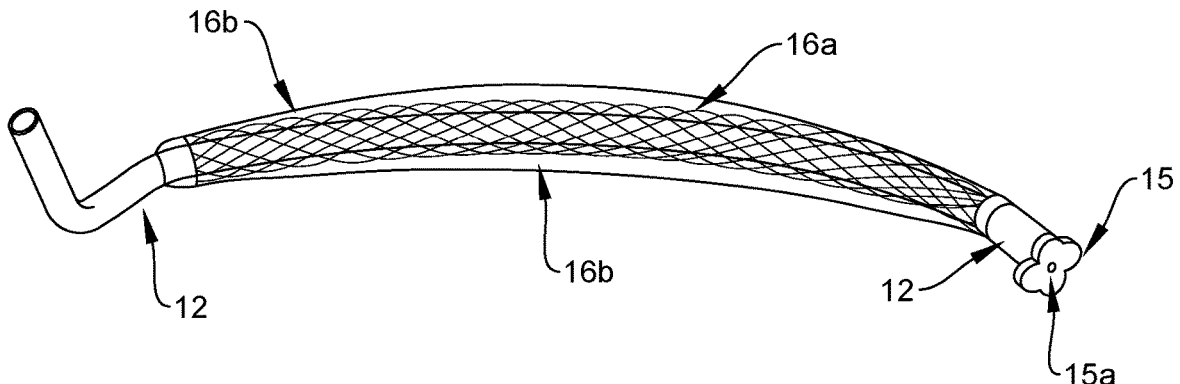
FIG. 12B is a perspective view of the spacer body when contracted, consistent with the present disclosure.

FIG. 12A-B are perspective views of the croissant or crescent shaped spacer body 16 in its expanded and contracted state. The tricuspid valve leg 12 may be configured to be performed with a curve as illustrated. The size, shape and volume of the spacer body 16 may vary according to different sizes and shapes of a heart and a tricuspid valve.

According to one aspect, FIGS. 13A-D show another embodiment of two-tube spacer body 16 connected to two pieces of the tricuspid valve leg 12. The tricuspid valve leg 12 may include a proximal tricuspid-tube piece 12b and a distal tricuspid-tube piece 12a as illustrated. The proximal end of the spacer body may be configured to be attached to the proximal tricuspid-tube piece 12b, and the distal end of the spacer body 16 may configured to be attached to the distal tricuspid-tube piece 12a. In this configuration, the cerclage filament 18 may be configured to pass through the proximal tricuspid-tube piece 12b and the distal tricuspid-tube piece 12a, then exit through the stopper 15.

Figure 13A:
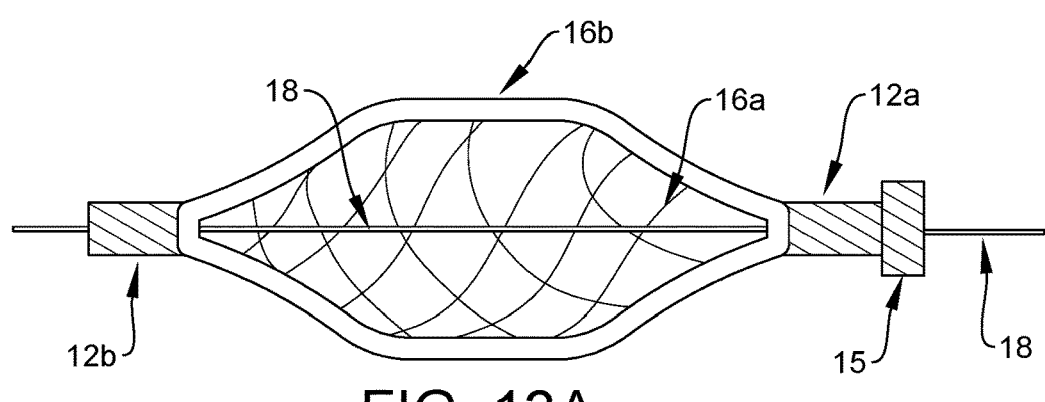
FIG. 13A depicts a side view of the spacer body when expanded, consistent with the present disclosure.
Figure 13B:
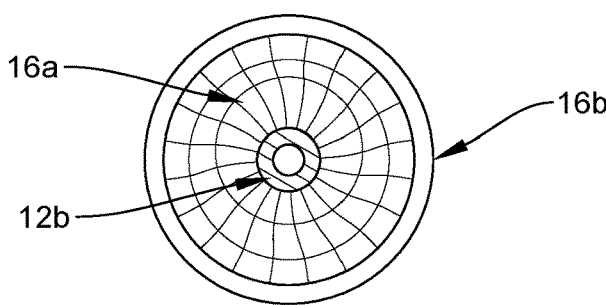
FIG. 13B depicts a cross-sectional view of the spacer body, consistent with the present disclosure.
Figure 13C:
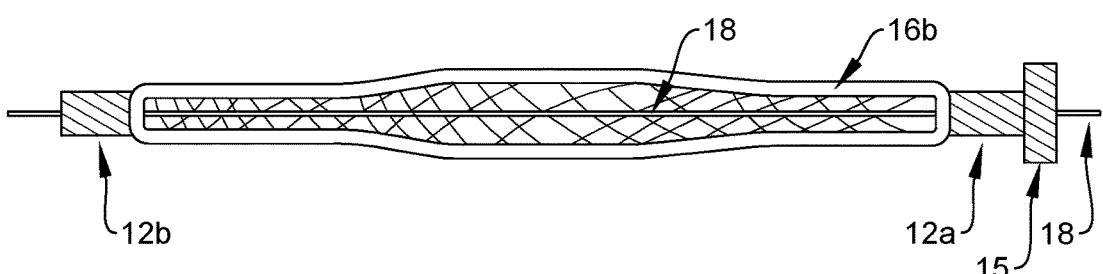
FIG. 13C depicts a side view of the spacer body when contracted, consistent with the present disclosure.
Figure 13D:
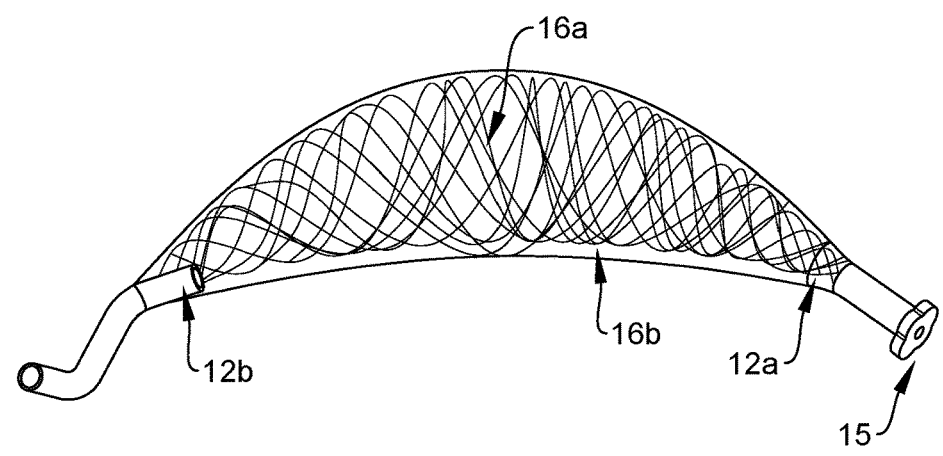
FIG. 13D is a perspective view of an embodiment of the spacer body consistent with the present disclosure.

FIG. 13C shows the two-tube spacer body 16 in a contracted state with the proximal tricuspid-tube piece 12b and the distal tricuspid-tube piece 12a. FIG. 13D shows a perspective view of the two-tube spacer body 16 expanded with the proximal tricuspid-tube piece 12b and the distal tricuspid-tube piece 12a.

Figure 14A:
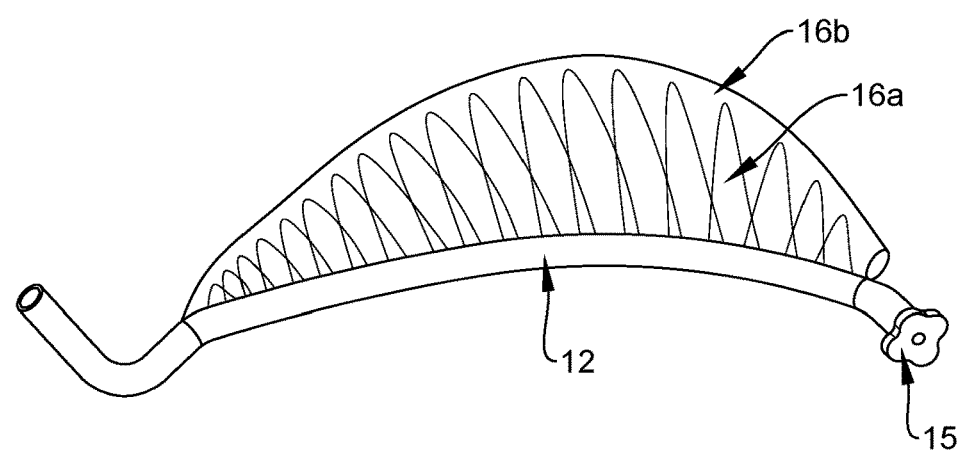
FIG. 14A is a perspective view of an embodiment of the spacer body consistent with the present disclosure.
Figure 14B:
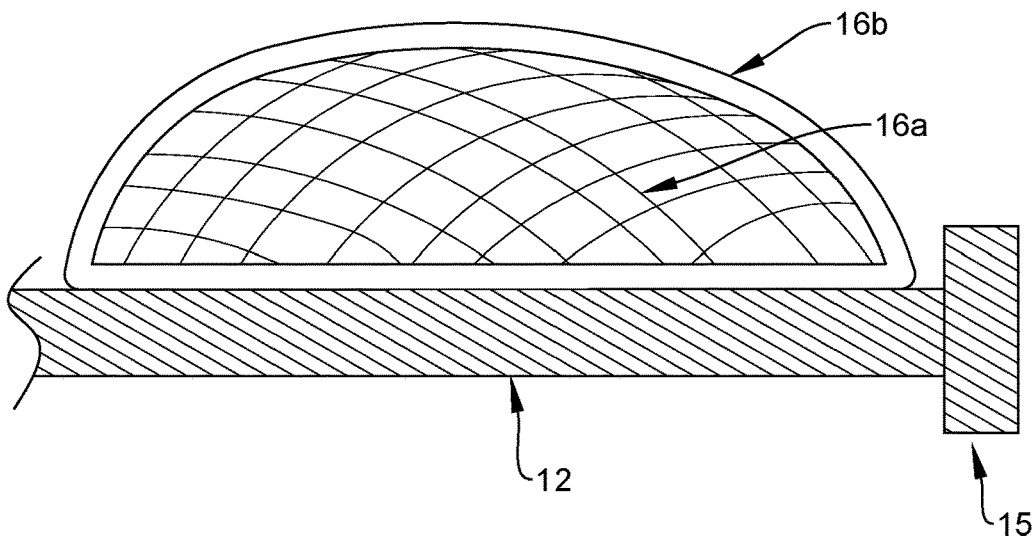
FIG. 14B is a side view of the embodiment of the spacer body consistent with the present disclosure.
Figure 14C:
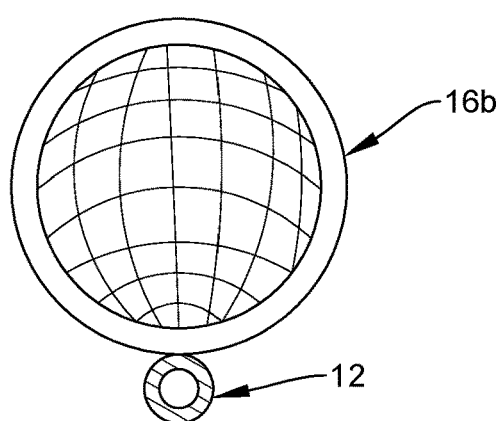
FIG. 14C is a cross-sectional view of the embodiment of the spacer body consistent with the present disclosure.

According to one aspect, the spacer body 16 may be configured to be attached on the surface of the defined distal portion of the tricuspid valve leg 12 as illustrated in FIGS. 14A-C. FIG. 14A is a perspective view of this embodiment. FIG. 14B shows a side view of this embodiment. FIG. 14C shows a cross-sectional view of the spacer body 16.

Figure 15A:
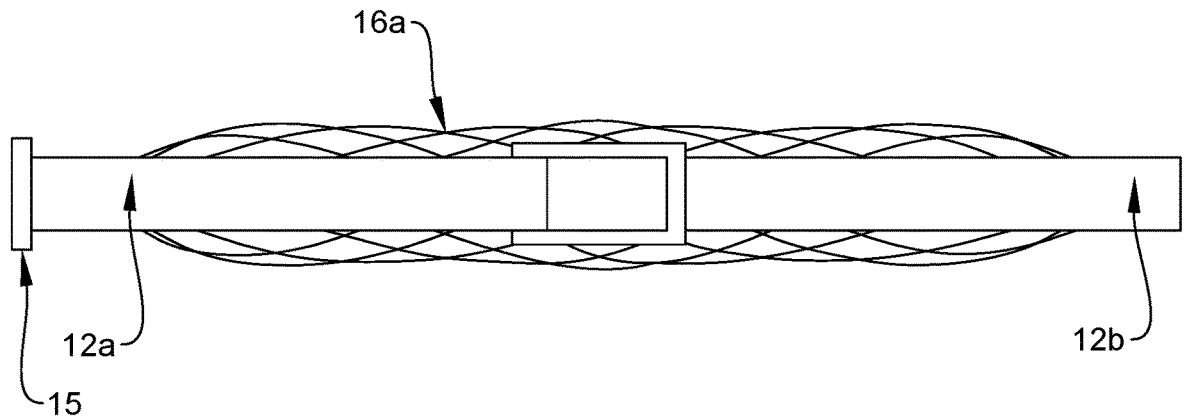
FIG. 15A shows an embodiment of the spacer body when the tricuspid valve leg is expanded consistent with the present disclosure.
Figure 15B:
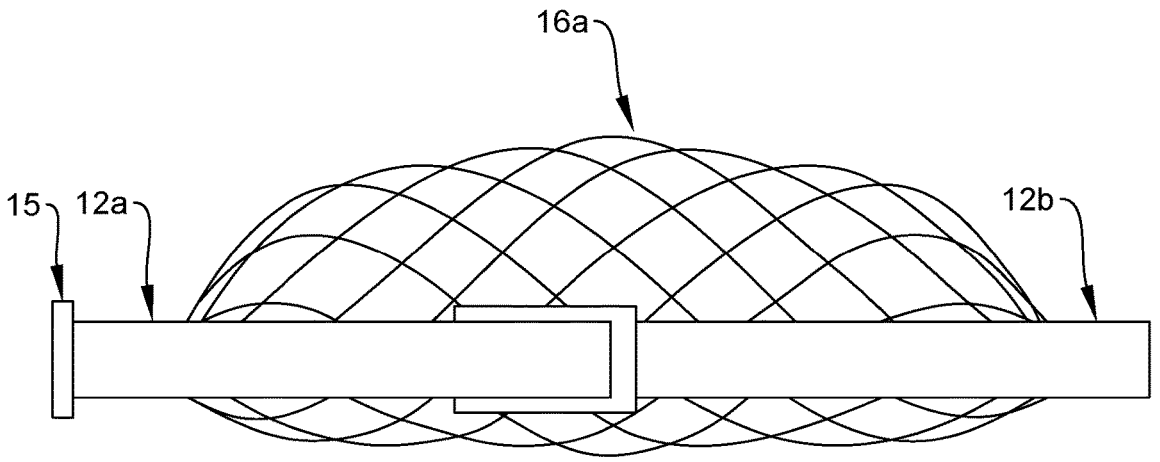
FIG. 15B shows an embodiment of the spacer body when the tricuspid valve leg is contracted consistent with the present disclosure.

According to one aspect, the spacer body of FIGS. 15A-B may be configured to be disposed on the two separated tubes of the tricuspid valve leg 12. As illustrated, the tricuspid valve legs 12 may include a distal piece 12a and a proximal piece 12b. The distal piece 12a may include a stopper 15 arranged at the end thereof. The stent 16a of the spacer body 16 may be arranged over the two pieces of the tricuspid valve leg 12. For example, the proximal end of the stent 16a may be configured to be securely attached onto the proximal piece 12b, and the distal end of the stent 16a may be configured to be securely attached onto the distal piece 12a as illustrated. Accordingly, the spacer body 16 may configured to expand or contract by the movement of the two pieces of the tricuspid valve leg 12.

Figure 16A:
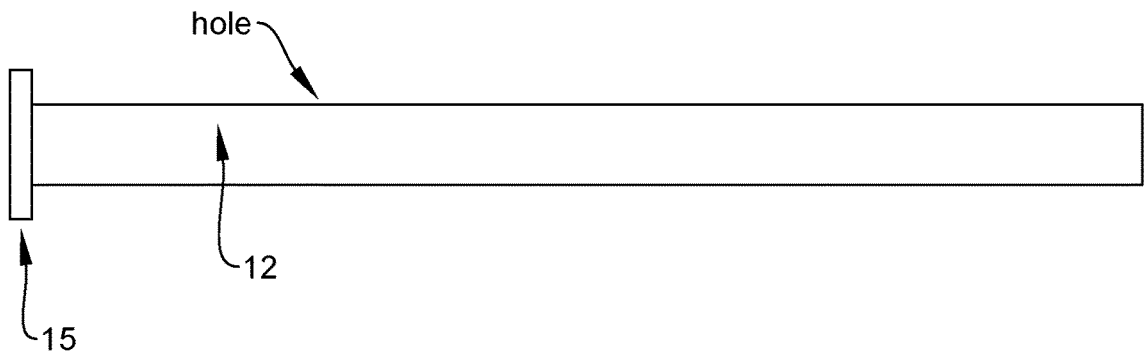
FIG. 16A depicts an embodiment of the tricuspid valve leg which includes a balloon consistent with the present disclosure.
Figure 16B:
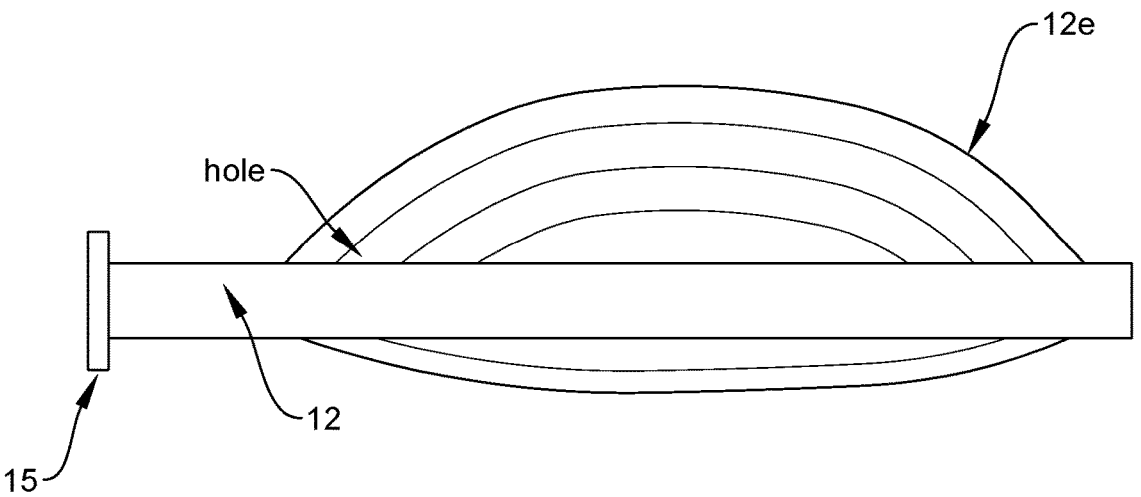
FIG. 16B depicts the embodiment of the tricuspid valve leg when the balloon expanded consistent with the present disclosure.

According to one aspect, the tricuspid valve leg 12 of FIGS. 16A-B may include a groove and a balloon therein. FIG. 16B shows the balloon 12e expanded as a balloon spacer body.

Figure 17A:
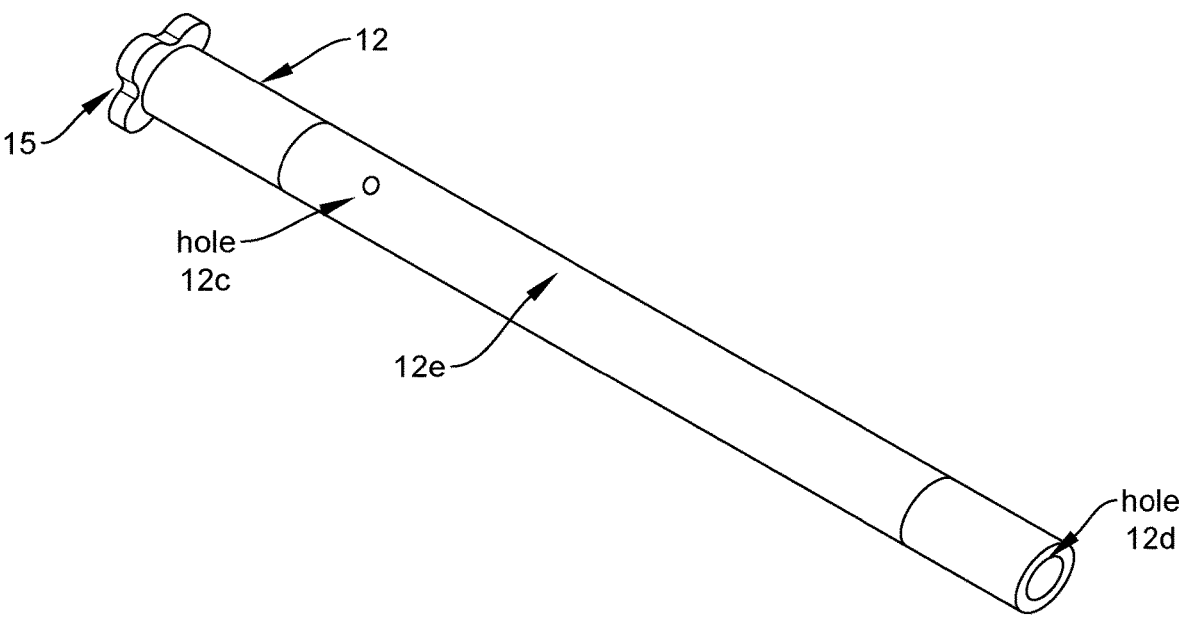
FIG. 17A is a perspective view of an embodiment of the balloon spacer body when contracted consistent with the present disclosure.
Figure 17B:
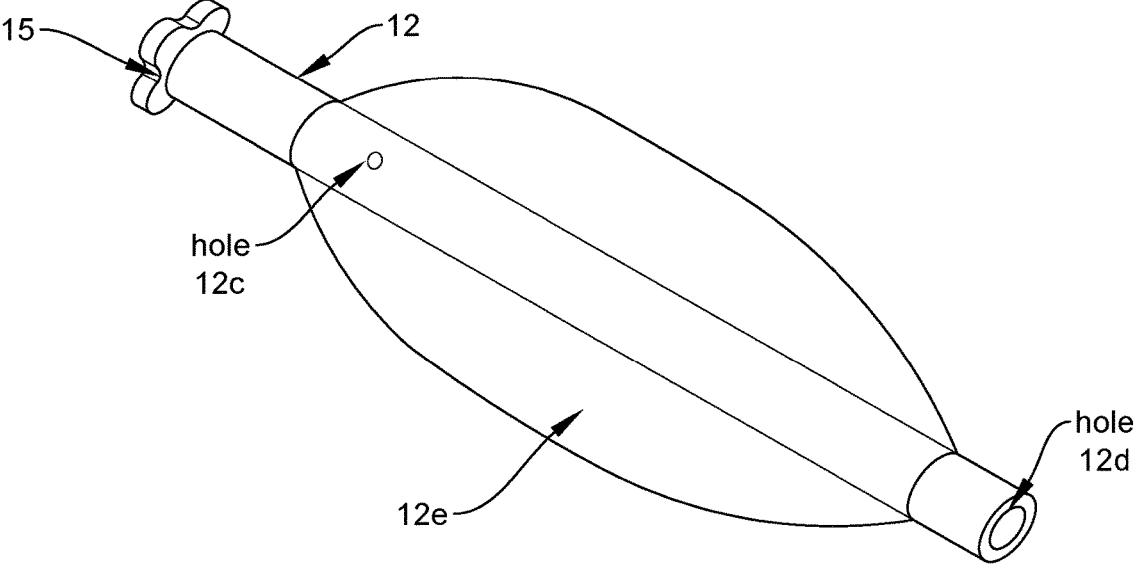
FIG. 17B is a perspective view of an embodiment of the balloon spacer body when expanded consistent with the present disclosure.

According to one aspect, another embodiment of the tricuspid valve leg 12 of FIGS. 17A-B may include a stopper 15 at the distal end, a distal hole 12c, a proximal hole 12d and a balloon 12e disposed on the surface thereof. The distal hole 12c may be configured to be connected to the proximal hole 12d such that the balloon 12e expands when air is supplied through the proximal hole 12d.

Figure 18A:
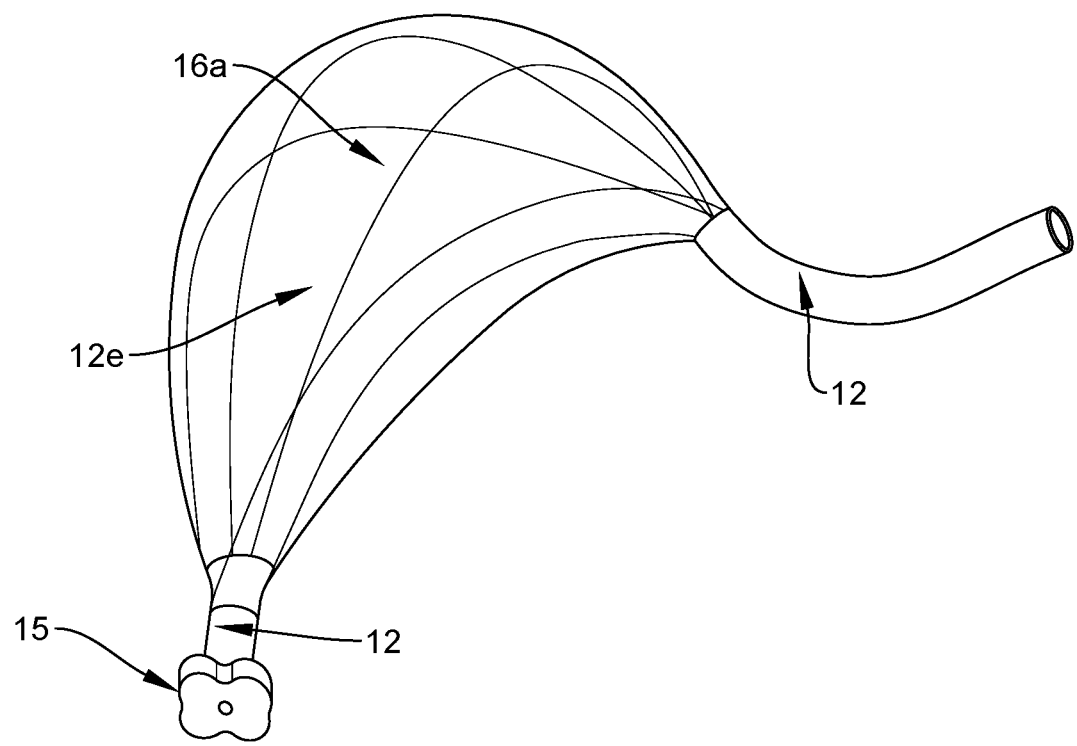
FIG. 18A is a perspective view of an embodiment of the balloon spacer body with a stent consistent with the present disclosure.

FIG. 18A shows a perspective view of another embodiment which may have a balloon 12e and a stent 16a within the balloon 12e.

Figure 18B:
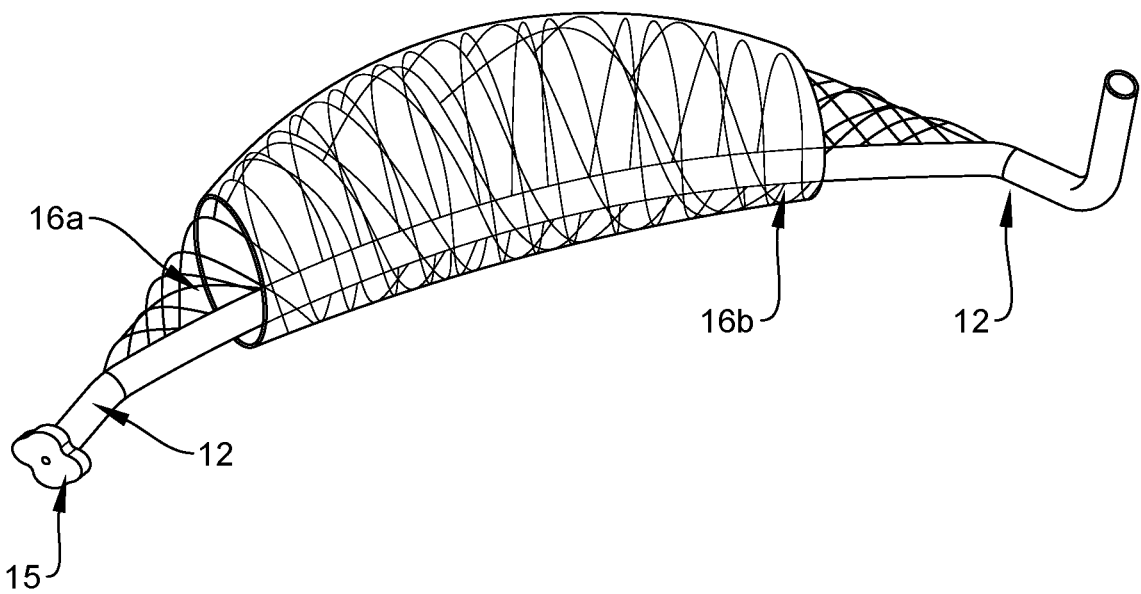
FIG. 18B is a perspective view of an embodiment of the spacer body which include a membrane partially covering the stent consistent with the present disclosure.

According to one aspect, another embodiment of the spacer body 16 of the FIG. 18B may include a membrane 16b which may partially cover a stent 16a such that the proximal and the distal ends of the stent 16a may be exposed.

Figure 19A:
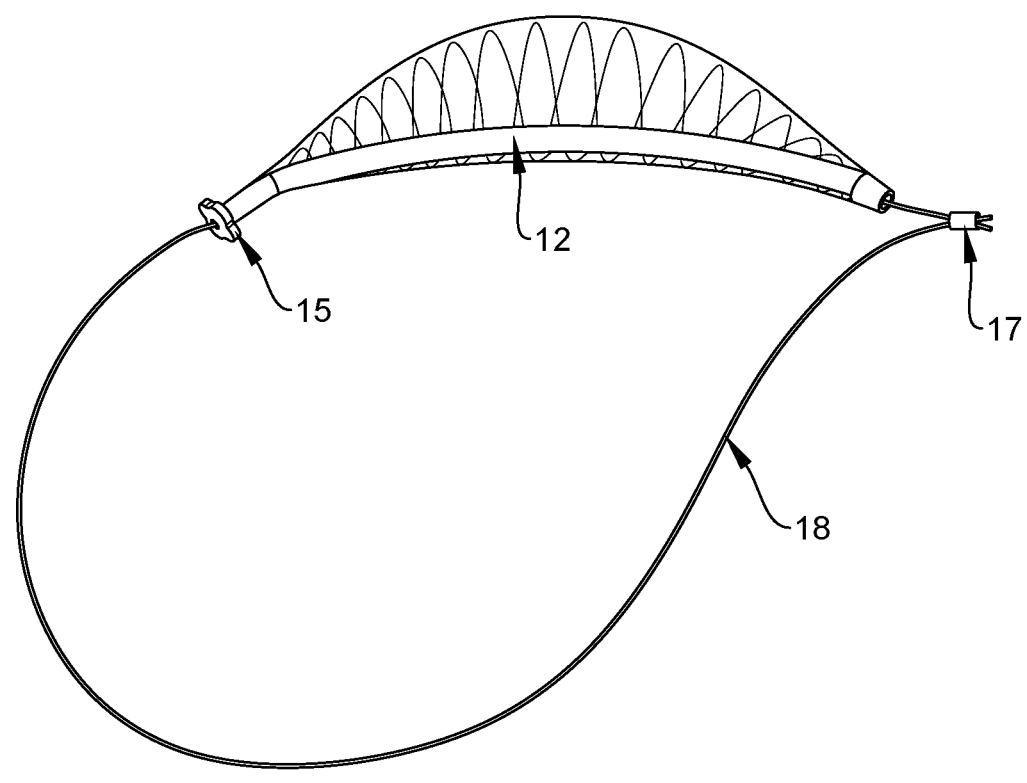
FIG. 19A is a perspective view of an embodiment of the transcatheter system which includes only the tricuspid valve leg consistent with the present disclosure.

According to one aspect, another embodiment of the transcatheter system 10 of FIG. 19A may include a tricuspid valve leg 12, a stopper 15, a spacer body 16, and a hinge ring 17. A cerclage filament 18 may be configured to pass through the hinge ring 17, the tricuspid valve leg 12, the spacer body 16, and the stopper 15.

Figure 19B:
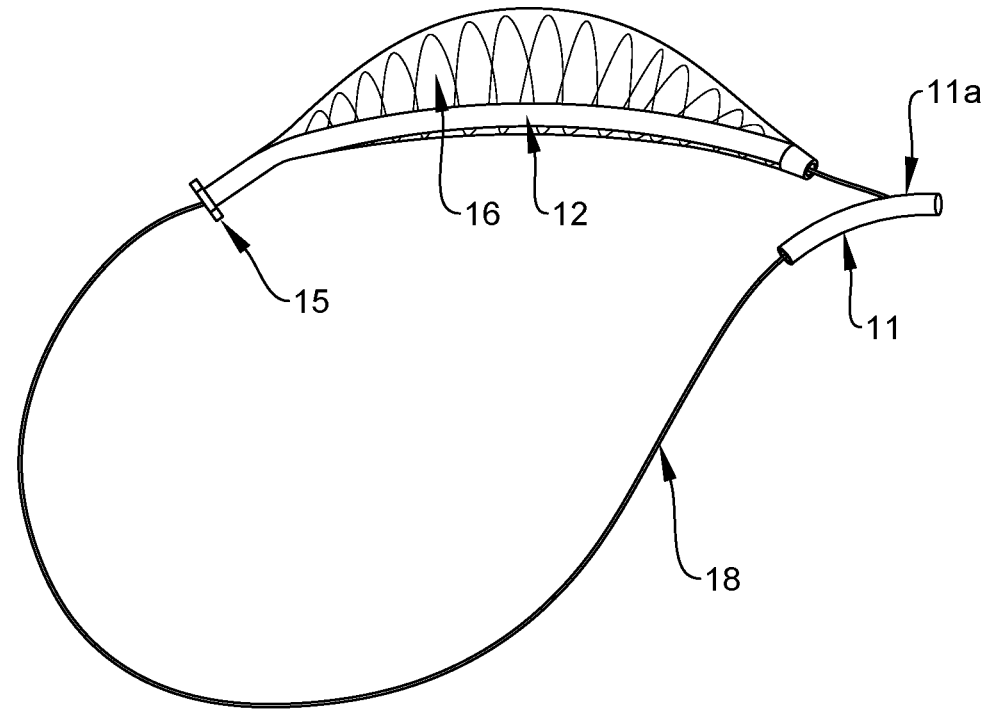
FIG. 19B is a perspective view of an embodiment of the transcatheter system which includes a separated coronary sinus leg consistent with the present disclosure.

FIG. 19B shows a perspective view of another embodiment of a transcatheter system 10 which may include a tricuspid valve leg 12 having a spacer body 16a, a stopper 15, and a coronary sinus leg 11. The coronary sinus leg 11 has a hole 11a on the surface thereof. A cerclage filament 18 may be configured to pass through the hole 11a of the coronary sinus leg 11, the tricuspid valve leg 12, the spacer body 16, the stopper 15, and return to the coronary sinus leg 11 as illustrated.

Figure 20:
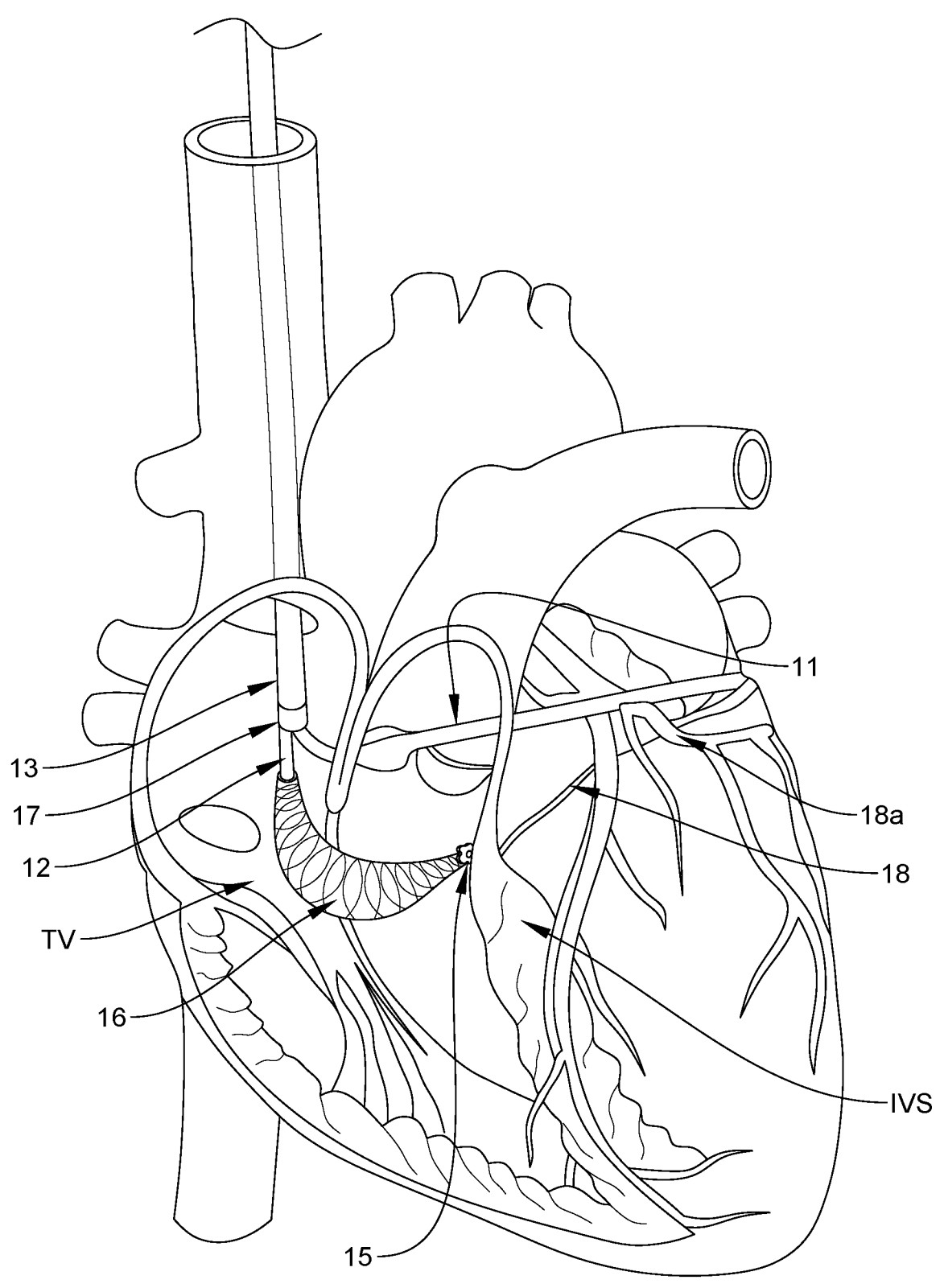
FIG. 20 shows the transcatheter system placed within the heart consistent with the present disclosure.
Figure 21:
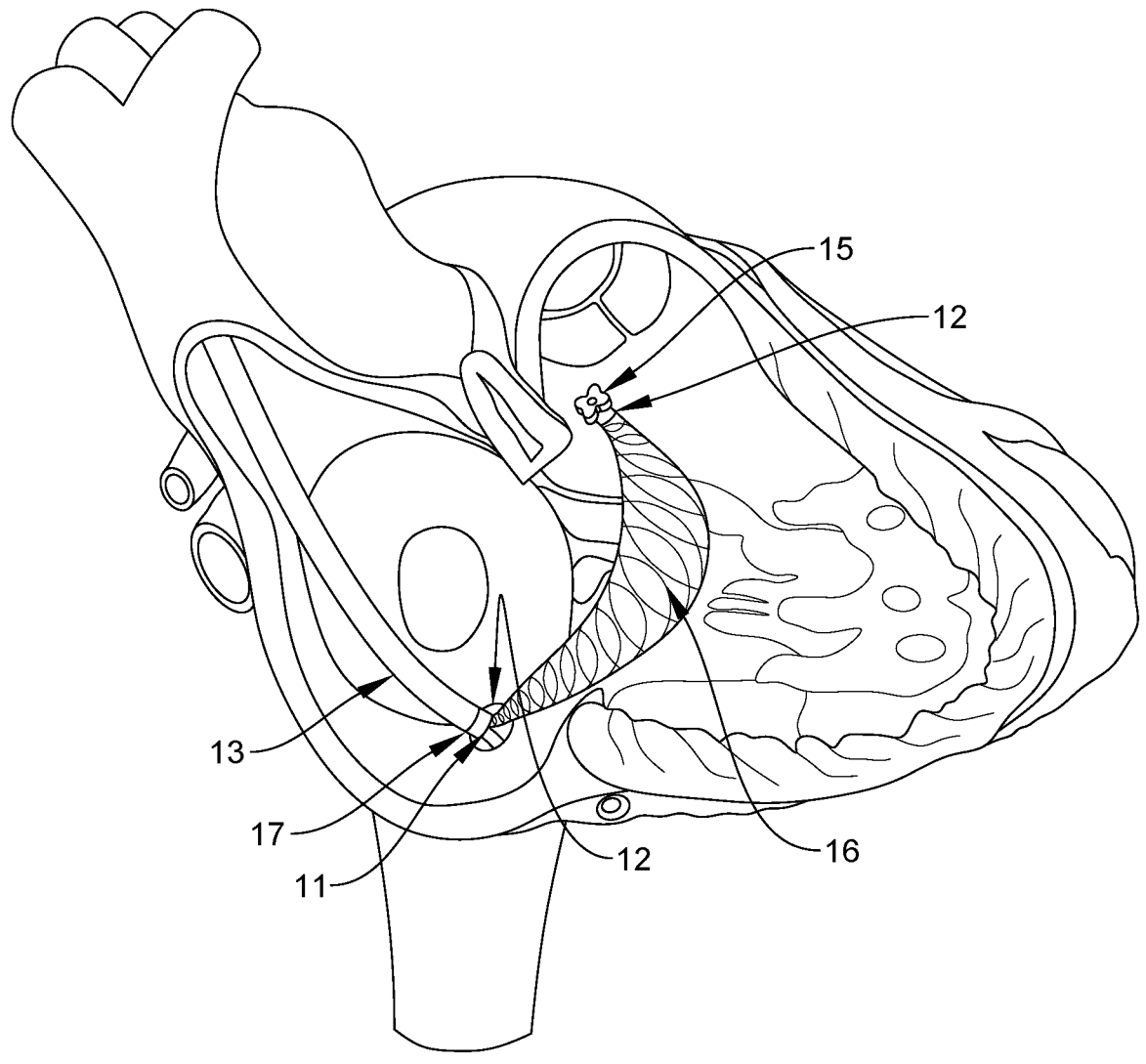
FIGS. 21-24 show perspective views from a different angle of the transcatheter system placed in the heart consistent with the present disclosure.
Figure 22:
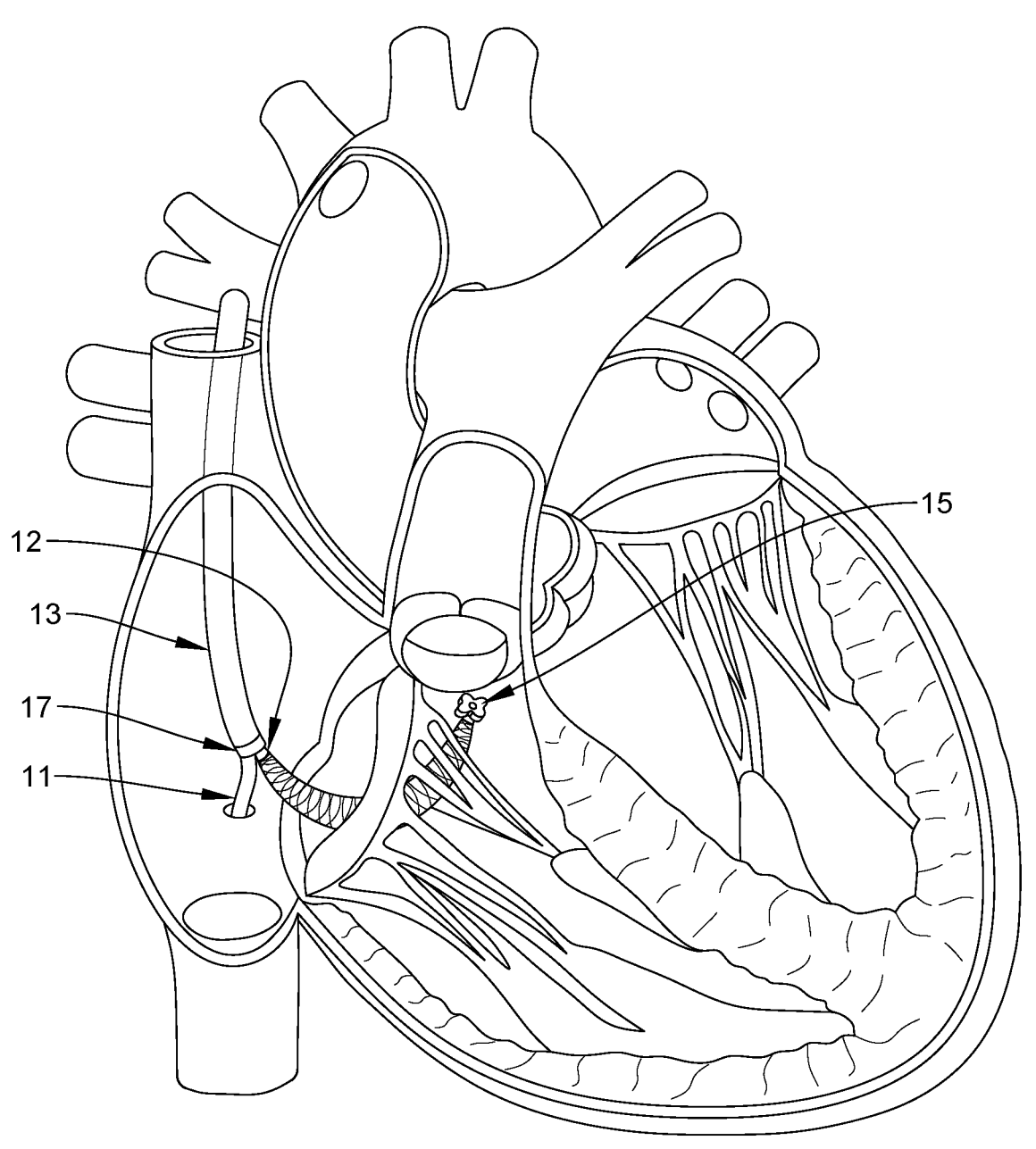

FIG. 20 shows the transcatheter system 10 placed within the heart. As illustrated, the juncture portion 14 or hinge ring 17 of the transcatheter system 10 may be configured to be positioned near or at the orifice of the coronary sinus. The coronary sinus leg 11 may be configured to extend through the coronary sinus and wrap around the mitral valve (MV). The tricuspid valve leg 12 having the spacer body 16 as shown may be configured to extend or traverse through the leaflets of the tricuspid valve (TV), and the distal end of the tricuspid valve leg 12 may be stopped by the stopper 15 against the interventricular septum (IVS). The portion of the tricuspid valve leg which may be defined from the juncture portion or the hinge ring to the stopper 15 may be configured to maintain a bent shape when the cerclage filament 18 has a proper tension. Accordingly, the spacer body 16, attached on the tricuspid valve leg 12, may be configured to block the regurgitation of the diseased tricuspid valve as illustrated in FIG. 9B.

Figure 23:
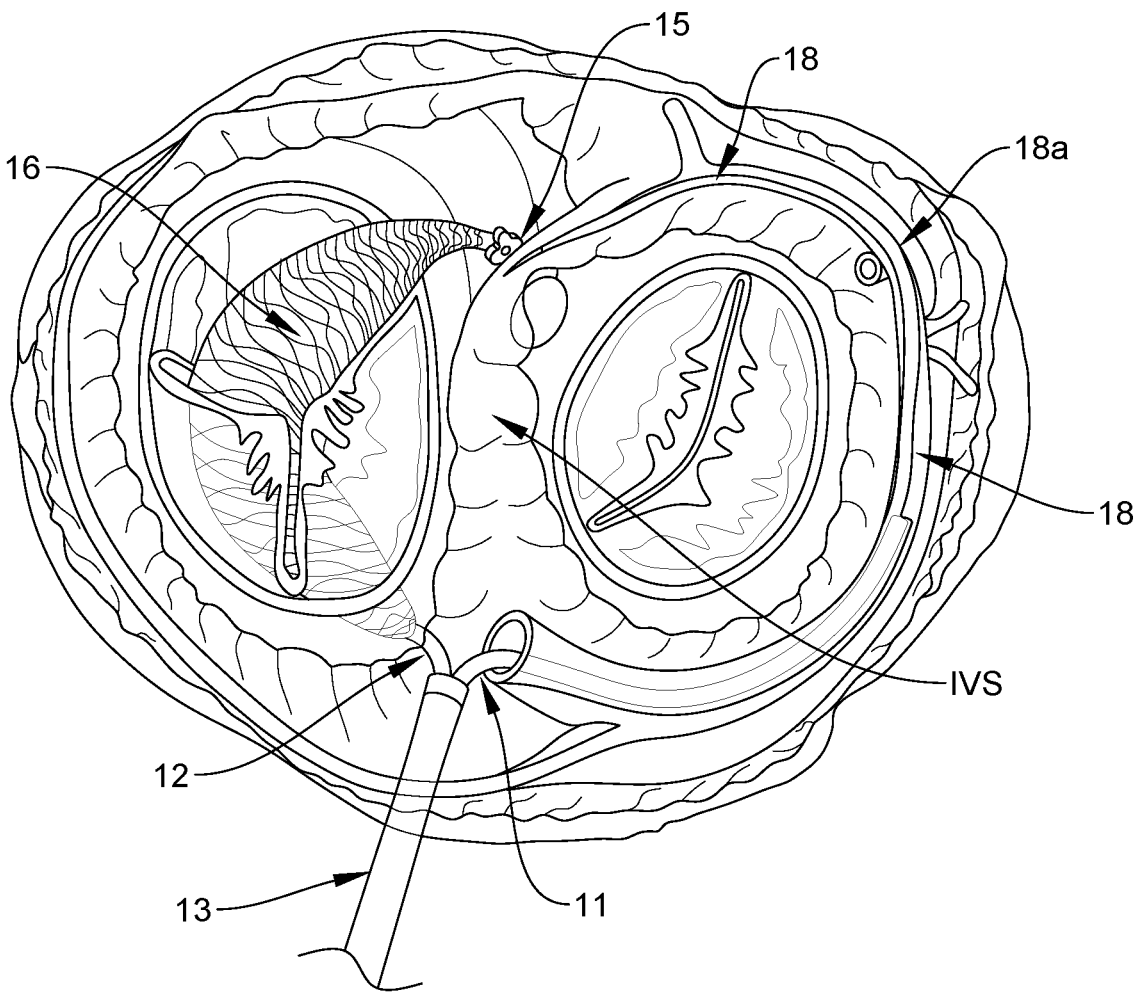
Figure 24:
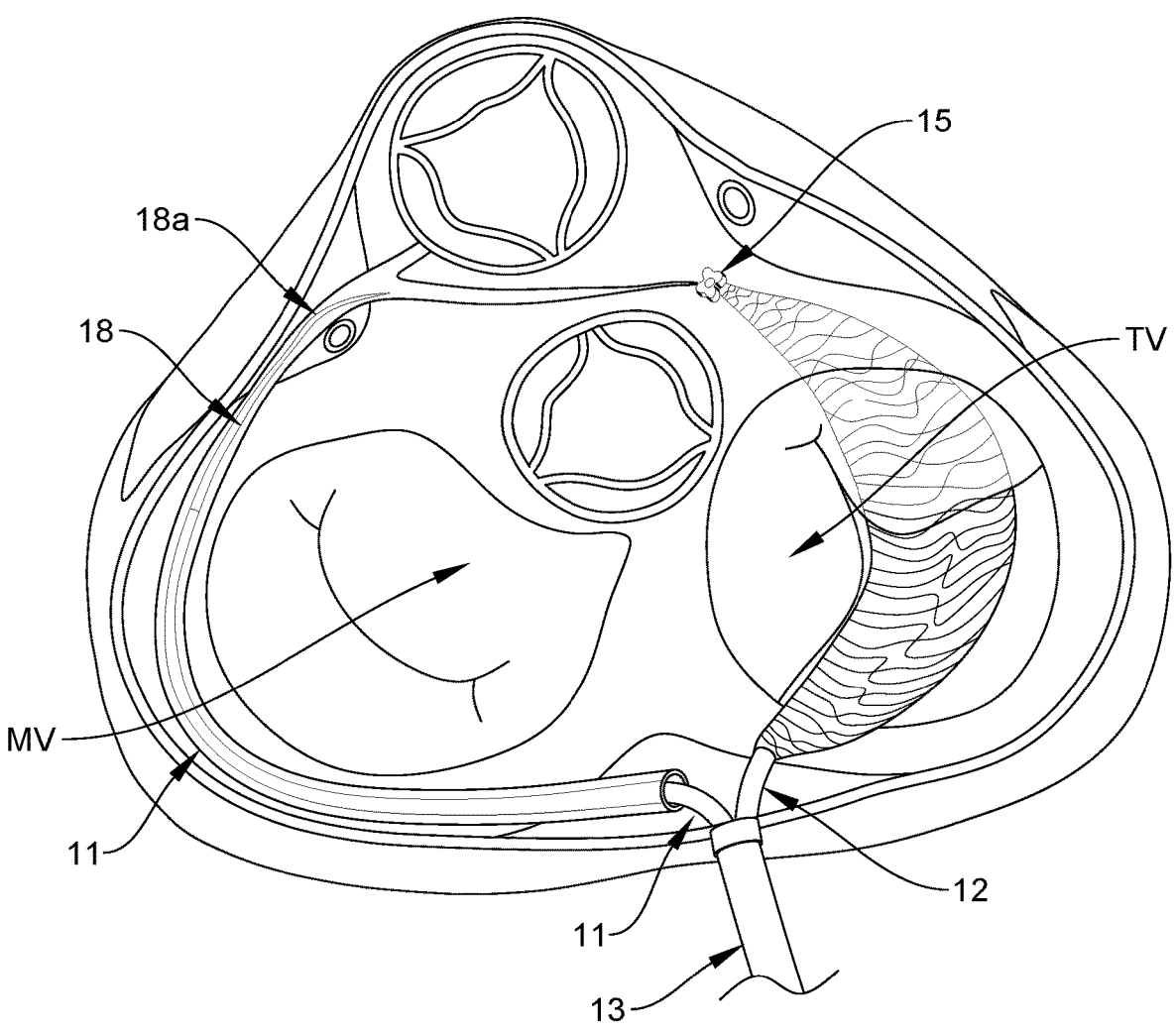

As illustrated in FIG. 20, the cerclage filament 18 may be configured to be disposed within the stem portion 13, the tricuspid valve leg 12, the stopper 15, and the coronary sinus leg 11 such that the cerclage filament 18 may create a loop through the coronary sinus across the interventricular septum (IVS), the coronary arteries, and the tricuspid valve under echocardiographic guidance as also illustrated in FIGS. 23-24.

FIGS. 21-24 show perspective views from a different angle of the transcatheter system 10 placed in the heart. The proximal portion of the spacer body 16 may be positioned in the atrial side of the tricuspid valve (TV) while the distal portion of the spacer body 16 may be positioned in the ventricle side of the tricuspid valve. The position, size and volume of the spacer body 16 may vary depending on the patient's situation. FIG. 23 depicts a perspective view from the ventral side. FIG. 24 depicts a perspective view from the atrial side.

Figure 25A:
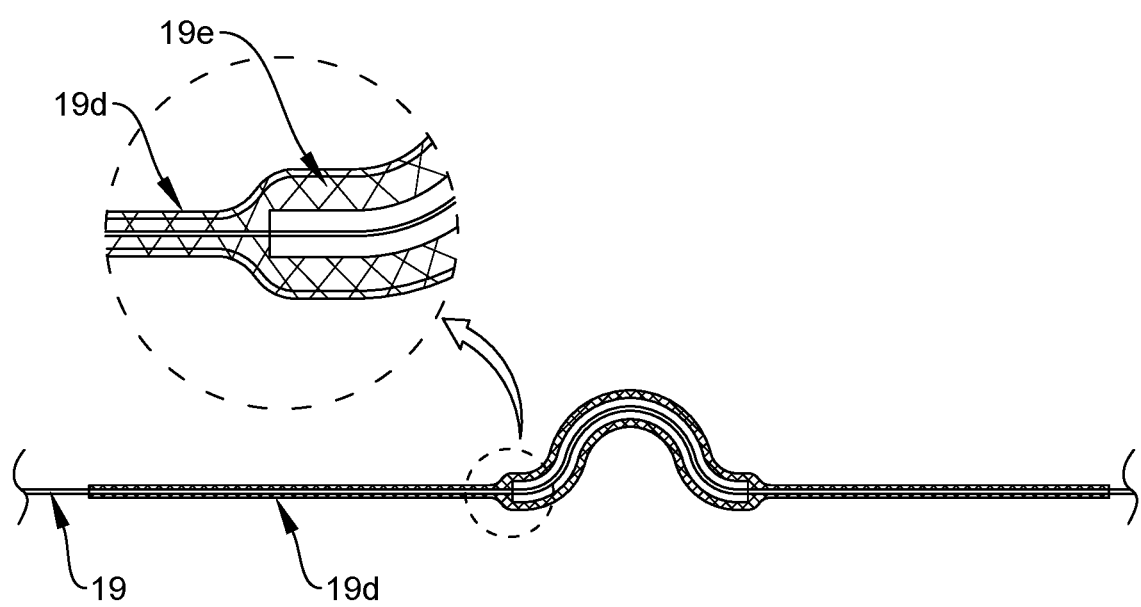
FIG. 25A depicts a side view of the cerclage filament consistent with the present disclosure.
Figure 25B:
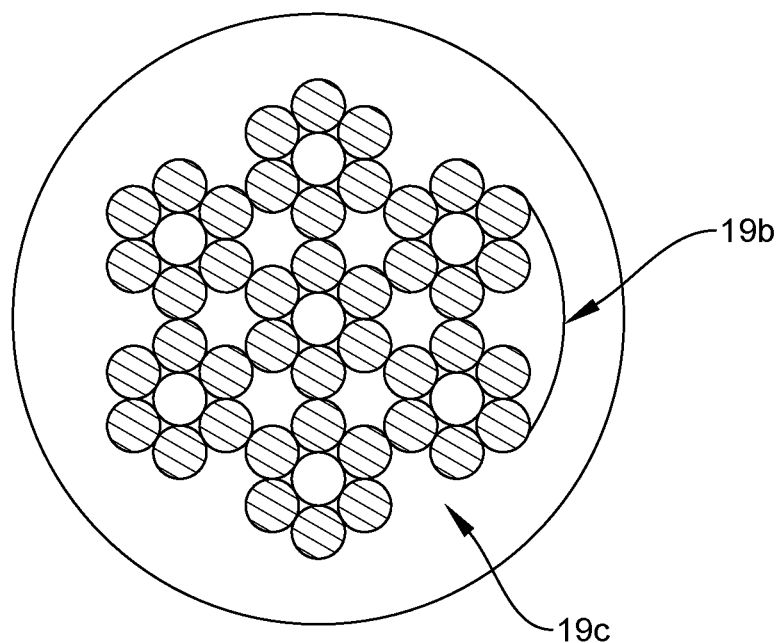
FIG. 25B depicts a cross-sectional view of the cerclage filament consistent with the present disclosure.

According to one aspect, the transcatheter system 10 may replace both cerclage filament 18 and the overpass part 18a entirely with the cerclage rope 19 as shown in FIG. 25A. The cerclage rope 19 may include stainless metal wires 19b therein and the coating 19c made of biocompatible nylon and covering the wires. The cerclage rope 19 may further include an arched coronary artery protector 19e. The cerclage rope 19 may further include the coating 19d integrating the arched coronary artery protector 19e by partially covering the coronary artery protector 19d. FIG. 25B is a cross-sectional view of the cerclage rope 19 showing the stainless metal wires 19b and the coating 19c.

Figure 26A:
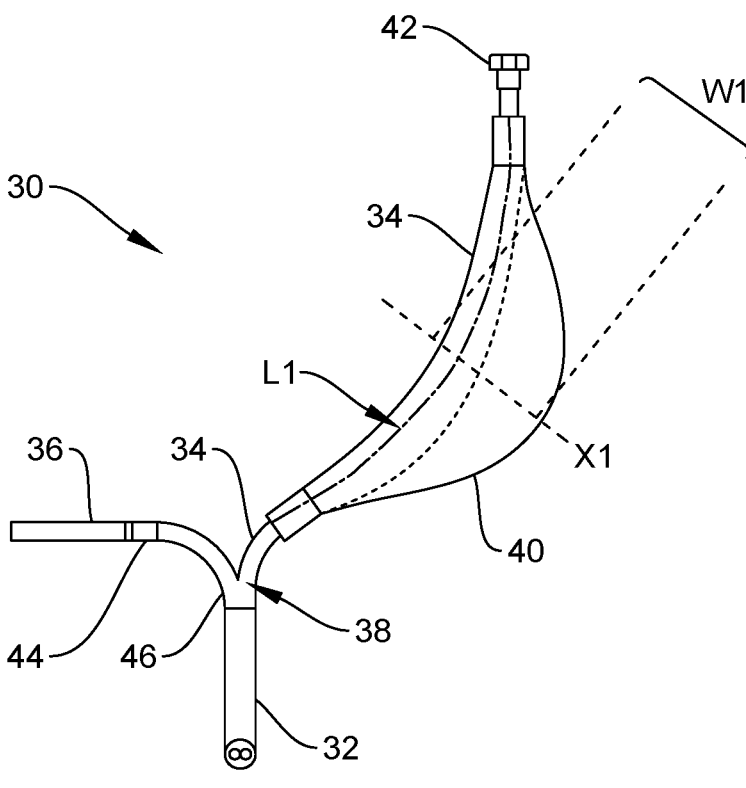
FIGS. 26A and 26B show an example cerclage assembly of this invention.
Figure 26B:
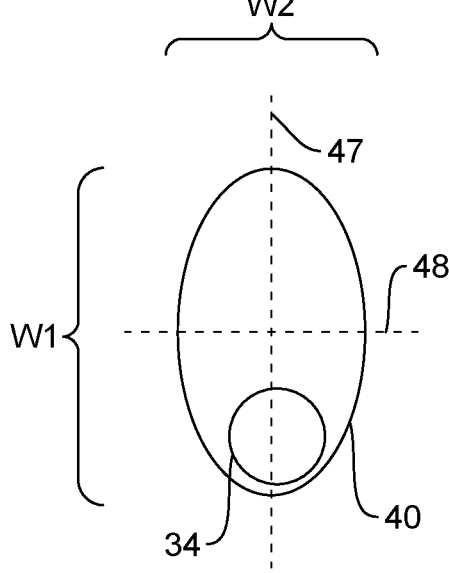

FIGS. 26A and 26B show an example cerclage assembly of this invention. FIG. 26A shows the cerclage assembly 30, which comprises a sleeve tube 46. The sleeve tube 46 comprises a main segment 32. At juncture 38, the sleeve tube 34 splits into a tricuspid leg 34 and a coronary sinus leg 36. Mounted on tricuspid valve leg 34 is a curved croissant-shaped spacer body 40. At the distal end of the tricuspid valve leg 34 is a stopper 42. There is also an anti-slip ring 44 on the coronary sinus leg 34 to improve anchoring within the coronary sinus.

FIG. 26A also demonstrates an example of how the length and width of the spacer body 40 is measured. Here, the croissant-shaped spacer body 40 is in relaxed configuration and its length is measured as the distance L1 along the tricuspid valve leg 34. L1 also represents the longitudinal axis of the spacer body 40. For measurements purposes, there is also a plane X1 where the spacer body 40 has greatest width in relaxed configuration. Plane X1 is orthogonal to the longitudinal axis of the tricuspid valve leg 34. FIG. 26B shows a cross-section of spacer body 40 along plane X1 to demonstrate how widths are measured. There is a width W1 along a line 47 of greatest width of spacer body 40. There is also a width W2 along a line 48 that is orthogonal to the line for width W1. As seen here, width W1 is greater than width W2.

According to another aspect, the present disclosure features a method of introducing a transcatheter system 10 with respect to a heart valve as following: a step of inserting a main sheath through the left subclavian vein or the right jugular vein or through the femoral vein; a step of passing a guidewire from the right atrium, the coronary sinus, the septal traversal (with or without septal vein), and the RVOT septum; a step of capturing the wire exiting the RVOT and reentering the captured wire into the right atrium; a step of pulling the guidewire toward the right atrium; a step of exchanging the guidewire with a cerclage filament 18; a step of pulling both ends of the cerclage filament out of the main sheath; a step of inserting or pushing the transcatheter system 10 over the cerclage filament 18; a step of placing the transcatheter system 10 in the heart; a step of adjusting a proper tension on the cerclage filament 18 for the transcatheter system 10 and adjusting the position of the transcatheter system 10 while monitoring with an echocardiogram; and a step of locking the cerclage filament 18 when the transcatheter system 10 is positioned as intended.

The descriptions and examples given herein are intended merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

The invention claimed is:

1. A method of treating tricuspid valve regurgitation in a patient's heart, comprising:
having a cerclage filament;
having a sleeve tube comprising;
(a) a main segment;
(b) a coronary sinus leg;
(c) a tricuspid valve leg;
(d) a spacer body mounted on the tricuspid valve leg;
wherein the tricuspid valve leg is longer than the coronary sinus leg;
wherein the main segment is longer than the tricuspid valve leg and longer than the coronary sinus leg;
making a vascular entry site into an entry vein;
inserting the cerclage filament through the vascular entry site and entry vein, and further into the patient's heart such that it takes a path into a right atrium, through a coronary sinus, through a great cardiac vein, out into a right ventricle, through a tricuspid valve, back into the right atrium, back through the entry vein, and exit back out of the vascular entry site;
sliding the sleeve tube onto the cerclage filament;
advancing the sleeve tube towards the patient's right atrium;
positioning the spacer body between leaflets of the patient's tricuspid valve;
creating a locked cerclage loop by fastening together an entry segment of the cerclage filament to an opposing return segment of the cerclage filament, wherein the fastening together occurs at a location outside the right atrium wherein the entry vein is a femoral vein and the cerclage filament passes through an inferior vena cava of the patient;
wherein the fastening together occurs at a location in the inferior vena cava at a position superior to a renal vein of the patient; and
wherein a proximal end of the sleeve tube terminates at a location in the inferior vena cava at a position superior to a renal vein of the patient.

2. The method of claim 1, wherein the path of the cerclage filament also includes a septal perforator vein of the patient.

3. The method of claim 1, further comprising the steps of:
inserting a guidewire through the vascular entry site and advancing the guidewire into the right atrium of the patient;
inserting a distal end of the guidewire into the coronary sinus of the patient;
advancing the guidewire and exiting the distal end of the guidewire into the right ventricle of the patient;
grasping the guidewire and pulling the distal end of the guidewire out of the entry vein;
exchanging the guidewire with the cerclage filament such that the cerclage filament takes the path through the patient's heart.

4. The method of claim 3, wherein the step of exchanging the guidewire with the cerclage filament comprises attaching a distal end of the cerclage filament to a proximal end of the guidewire and pulling the guidewire out such that the cerclage filament follows the path created by the guidewire.

5. The method of claim 1, further comprising the steps of:
sliding the coronary sinus leg over one of the entry segment or the return segment of the cerclage filament;
sliding the tricuspid valve leg over the other of the entry segment or the return segment of the cerclage filament.

6. The method of claim 1, wherein the step of positioning the spacer body is performed while monitoring with an echocardiogram.

7. The method of claim 1, further comprising anchoring the cerclage loop at an anchoring site in the patient's body.

8. The method of claim 1, wherein the step of advancing the sleeve tube comprises inserting the coronary sinus leg into the patient's coronary sinus in the right atrium and inserting the tricuspid valve leg through the patient's tricuspid valve.

9. The method of claim 1, wherein the cerclage filament further comprises an overpass arch and the method further comprises the step of positioning the overpass arch inside the great cardiac vein at a position over a coronary artery.

10. The method of claim 1, wherein the spacer body provides a coaptation surface for leaflets of the tricuspid valve.

11. The method of claim 1, wherein the sleeve tube further comprises a stopper located at a distal end of the tricuspid valve leg, and wherein the method further comprises positioning the stopper against a wall of the right ventricle of the patient.

* * * * *